US010730939B2

(12) United States Patent
Fujita et al.

(10) Patent No.: US 10,730,939 B2
(45) Date of Patent: Aug. 4, 2020

(54) ANTI-AGGRUS MONOCLONAL ANTIBODY, DOMAIN IN AGGRUS WHICH IS REQUIRED FOR BINDING TO CLEC-2, AND METHOD FOR SCREENING FOR AGGRUS-CLEC-2 BINDING INHIBITOR

(71) Applicant: JAPANESE FOUNDATION FOR CANCER RESEARCH, Tokyo (JP)

(72) Inventors: Naoya Fujita, Tokyo (JP); Takaya Sekiguchi, Tokyo (JP); Satoshi Takagi, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 40 days.

(21) Appl. No.: 15/744,507

(22) PCT Filed: Jul. 11, 2016

(86) PCT No.: PCT/JP2016/070466
§ 371 (c)(1),
(2) Date: Jan. 12, 2018

(87) PCT Pub. No.: WO2017/010463
PCT Pub. Date: Jan. 19, 2017

(65) Prior Publication Data
US 2018/0237518 A1    Aug. 23, 2018

(30) Foreign Application Priority Data

Jul. 15, 2015 (JP) .................. 2015-140998
Oct. 28, 2015 (JP) .................. 2015-211883

(51) Int. Cl.
| | | |
|---|---|---|
| A61K 39/00 | (2006.01) | |
| C07K 16/28 | (2006.01) | |
| C07K 7/06 | (2006.01) | |
| C12N 15/02 | (2006.01) | |
| C07K 16/30 | (2006.01) | |
| A61P 35/00 | (2006.01) | |
| G01N 33/574 | (2006.01) | |

(52) U.S. Cl.
CPC .............. *C07K 16/28* (2013.01); *A61P 35/00* (2018.01); *C07K 7/06* (2013.01); *C07K 16/30* (2013.01); *C12N 15/02* (2013.01); *G01N 33/574* (2013.01); *A61K 2039/505* (2013.01); *C07K 2317/14* (2013.01); *C07K 2317/24* (2013.01); *C07K 2317/34* (2013.01); *C07K 2317/76* (2013.01); *C07K 2317/92* (2013.01)

(58) Field of Classification Search
CPC .................................................. C07K 16/28
See application file for complete search history.

(56) References Cited

U.S. PATENT DOCUMENTS

2014/0235827 A1   8/2014   Fujita et al.
2016/0347834 A1   12/2016  Kato et al.

FOREIGN PATENT DOCUMENTS

| JP | 2004-350677 | 12/2004 |
| JP | 2013-71916 | 4/2013 |
| WO | 2012/128082 | 9/2012 |
| WO | 2015/053381 | 4/2015 |

OTHER PUBLICATIONS

Oki et al Monoclonal Antibodies in Immunodiagnosis and Immunotherapy vol. 34 p. 174 (Jun. 2015). (Year: 2015).*
Kato et al, Oncotarget, vol. 6 p. 36003 (2015) (Year: 2015).*
Extended European Search Report dated Jan. 28, 2019, Application No. 16824443.2, 10 pages.
Youya Nakazawa et al: "Prevention of hematogenous metastasis by neutralizing mice and its chimeric anti-Aggrus/podoplanin antibodies", Cancer Science, Japanese Cancer Association, Nov. 1, 2011 (Nov. 1, 2011), vol. 102, No. 11, pp. 2051-2057, XP002732562, ISSN:1347-9032, DOI:10.1111/ J.1349-7006.2011.02058.X, Tokyo, JP.
Satoshi Ogasawara et al: "Characterization of Anti-podoplanin Monoclonal Antibodies: Critical Epitopes for Neutralizing the Interaction Between Podoplanin and CLEC-2", Hybridoma, Aug. 1, 2008 (Aug. 1, 2008), vol. 27, No. 4, pp. 259-267, XP055024221, ISSN:1554-0014, DOI:10.1089/hyb.2008.0017.
Kato, et al. "Molecular Identification of Aggrus/T1α as a Platelet Aggregation-inducing Factor Expressed in Colorectal Tumors", 2003, Journal of Biological Chemistry, vol. 278, p. 51599-51605, 8 pages.
Kato, et al. "Enhanced Expression of Aggrus (T1alpha/Podoplanin), a Platelet-Aggregation-Inducing Factor in Lung Squamous Cell Carcinoma", 2005, Tumor Biology, vol. 26, p. 195-200, 6 pages.
Martin-Villar, et al. "Characterization of Human PA2.26 antigen )T1α-2, podoplanin), a small membrane mucin induced in oral squamous cell carcinomas", 2005, Int. J. Cancer, vol. 113, p. 899-910, 13 pages.

(Continued)

*Primary Examiner* — Sheela J. Huff
(74) *Attorney, Agent, or Firm* — Rankin, Hill & Clark LLP

(57) ABSTRACT

A novel domain of Aggrus involved in the binding to CLEC-2 was searched for, and monoclonal antibodies recognizing the domain were obtained. The newly found PLAG4 domain is important for Aggrus binding to CLEC-2. Monoclonal antibodies recognizing this region were further developed. The present invention can provide novel Aggrus-CLEC-2 binding inhibitors, platelet aggregation inhibitors, cancer metastasis inhibitors, and tumor growth inhibitors using these antibodies.

8 Claims, 17 Drawing Sheets

Specification includes a Sequence Listing.

(56) References Cited

OTHER PUBLICATIONS

Yuan, et al. "Overexpression of Podoplanin in Oral Cancer and Its Association with Poor Clinical Outcome", 2006, Cancer, vol. 107, p. 563-569, 7 pages.
Wicki, et al. "Tumor Invasion in the absence of epithelial-mesenchymal transition: Podoplanin-mediated remodeling of the actin cytoskeleton", 2006, Cancer Cell, vol. 9, p. 261-272, 12 pages.
Kimura, et al. "Podoplanin as a marker for mesothelioma", 2005, Pathology International, vol. 55, p. 83-86, 4 pages.
Fukunaga, "Expression of D2-40 in lymphatic endothelium of normal tissues and in vascular tumours", 2005, Histopathology, vol. 46, p. 396-402, 8 pages.
Kato, et al., "Aggrus: a diagnostic marker that distinguishes seminoma from embryonal carcinoma in testicular germ cell tumors", 2004, Oncogene, vol. 23, p. 8552-8556, 5 pages.
Mishima, et al.,"Podoplanin expression in primary central nervous system germ cell tumors: a useful histological marker for the diagnosis of germinoma", 2006, Acta Neuropathol, vol. 111, p. 563-568, 6 pages.
Mishima, et al. "Increased expression of podoplanin in malignant astrocytic tumors as a novel molecular marker of malignant progression", 2006, Acta Neuropathol, vol. 111, p. 483-488, 6 pages.
Kunita, et al., The Platelet Aggregation-Inducing Factor Aggrus/Podoplanin Promotes Pulmonary Metastasis, 2007, American Journal of Pathology, vol. 170, p. 1337-1347, 11 pages.
Takagi, et al., "Expression of Aggrus/podoplanin in bladder cancer and its role in pulmonary metastasis", 2014, International Journal of Cancer, vol. 134, p. 2605-2614, 11 pages.
Suzuki-Inoue, et al. "Involvement of the Snake Toxin Receptor CLEC-2, in Podoplanin-mediated Platelet Activation, by Cancer Cells", 2007, Journal of Biological Chemistry, vol. 282, p. 25993-26001,10 pages.
Fujita, et al. "The impact of Aggrus/Podoplanin on platelet aggregation and tumour metastasis", 2012, Journal of Biochemistry, vol. 152, p. 407-413, 7 pages.
Nagae, et al. "A Platform of C-type Lectin-like Receptor CLEC-2 for Binding O-Glycosylated Podoplanin and Nonglycosylated Rhodocytin", 2014, Structure, vol. 22, p. 1711-1721, 11 pages.
Morrison, et al., "Chimeric human antibody molecules: Mouse antigen-binding domains with human constant region domains", 1984, Proc. Natl. Acad. Sci., USA, vol. 81, p. 6851-6855, 5 pages.
Jones, et al., "Replacing the complementarity—determining regions in a human antibody with those from a mouse", 1986, Nature, vol. 321, p. 522-525, 4 pages.
Amano, et al., "Engineering of mucin-type human glycoproteins in yeast cells", 2008, Proc. Natl. Acad. Sci., USA, vol. 105, p. 3232-3237, 6 pages.
Takagi, et al., "Platelets Promote Tumor Growth and Metastasis via Direct Interaction between Aggrus/Podoplanin and CLEC-2", 2013, PLOS One, vol. 8, e73609, 11 pages.
Oki, et al., "Characterization of Monoclonal Antibody LpMab-7 Recognizing Non-PLAG Domain of Podoplanin", Monoclonal Antibodies in Immunodiagnosis and Immunotherapy, 2015, vol. 34, No. 3, p. 174-180, 7 pages.
Oki, et al., "Characterization of Monoclonal Antibody LpMab-3 Recognizing Sialylated Glycopeptide of Podoplanin", Monoclonal Antibodies in Immunodiagnosis and Immunotherapy, 2015, vol. 34, No. 1, p. 44-50, 7 pages.
Kato, et al., "Development of a cancer-specific monoclonal antibody LpMab-2 specific for cancer-type podooplanin", Cancer Research, 2014, vol. 74 (19 Supplement) Abstract No. 663, 2 pages.
Kato, et al., Molecular analysis of the pathophysiological binding of the platelet aggregation-inducing factor podoplanin to the C-type lectin-like receptor CLEC-2; Cancer Sci., 2008, vol. 99 (1), p. 54-61, 8 pages.
Matsui, et al., "Epitope-Specific Antibodies to the 43-kD Glomerular Membrane Protein Podoplanin Cause Proteinuria and Rapid Flattening of Podocytes", Journal of the American Society of Nephrology, 1998, vol. 9, p. 2013-2026, 14 pages.
Zimmer, et al., "Molecular Characterization of gp40, a mucin-type glycoprotein from the apical plasma membrane of Madin-Darby canine kidney cells (type I)", Biochem, J., 1997, vol. 326, p. 99-108, 10 pages.
Sekiguchi, T., et al., "Targeting a novel domain in podoplanin for inhibiting platelet-mediated tumor metastasis", Oncotarget, 2016, vol. 7, No. 4, p. 3934-3946, 13 pages.
Kato, et al., "Novel Monoclonal Antibody LpMab-17 Developed by CasMab Technology Distinguishes Human Podoplanin from Monkey Podoplanin", Monoclonal Antibodies in Immunodiagnosis and Immunotherapy, 2016, vol. 35, No. 2, p. 109-116, 8 pages.
Written Opinion of the International Searching Authority, JP 2016/070466 dated Sep. 20, 2016, 11 pages.
International Search Report, JP 2016/070466 dated Sep. 20, 2016 4 pages.

\* cited by examiner

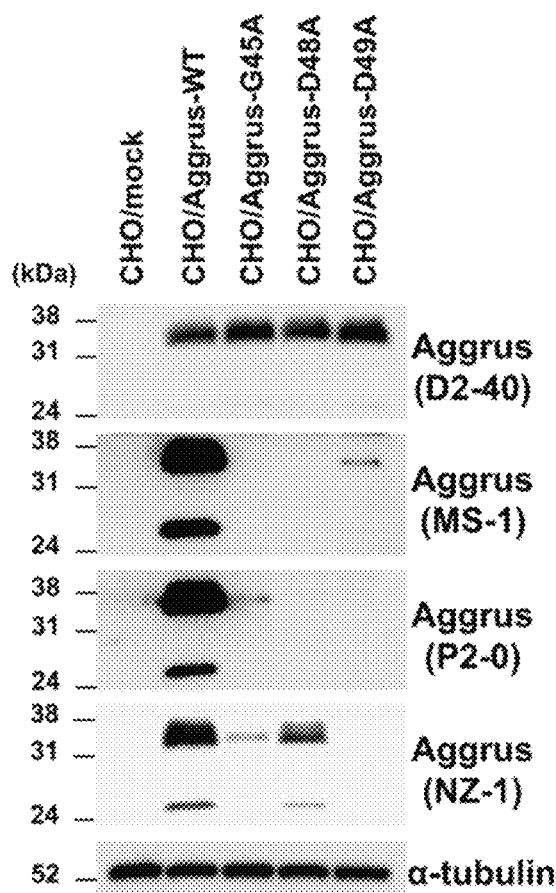

| | | |
|---|---|---|
| PLAG consensus: | E D X X V T P G | SEQ ID NO.15 |
| PLAG1 | 29-E D D T E T T G-36 | SEQ ID NO.16 |
| PLAG2 | 38-E G G V A M P G-45 | SEQ ID NO.17 |
| PLAG3 | 47-E D D V V T P G-54 | SEQ ID NO.18 |
| PLAG4 | 81-E D L – P T S E-87 | SEQ ID NO.19 |

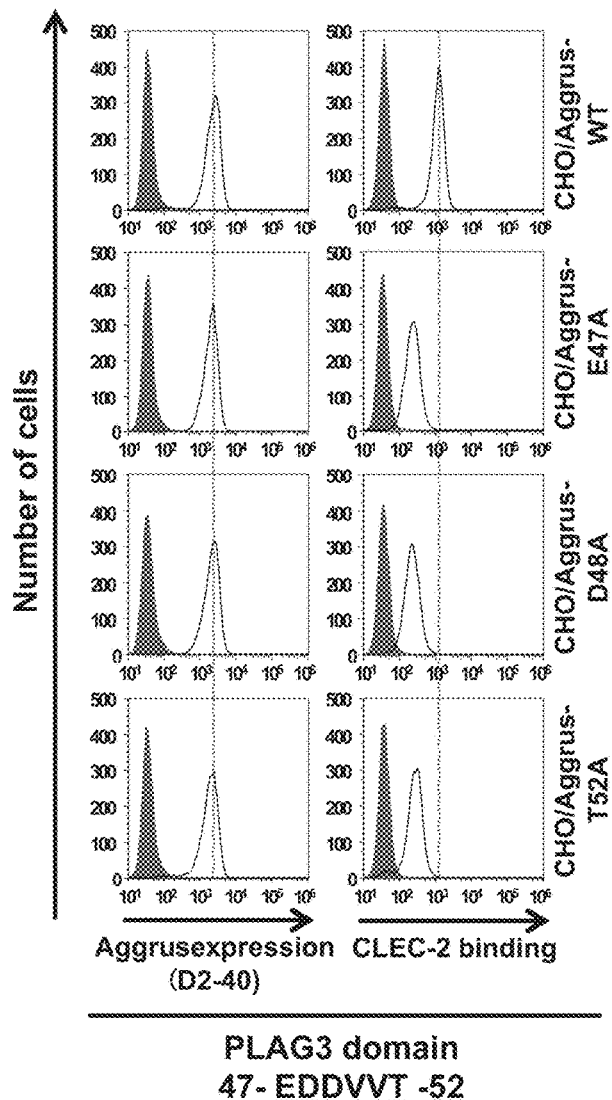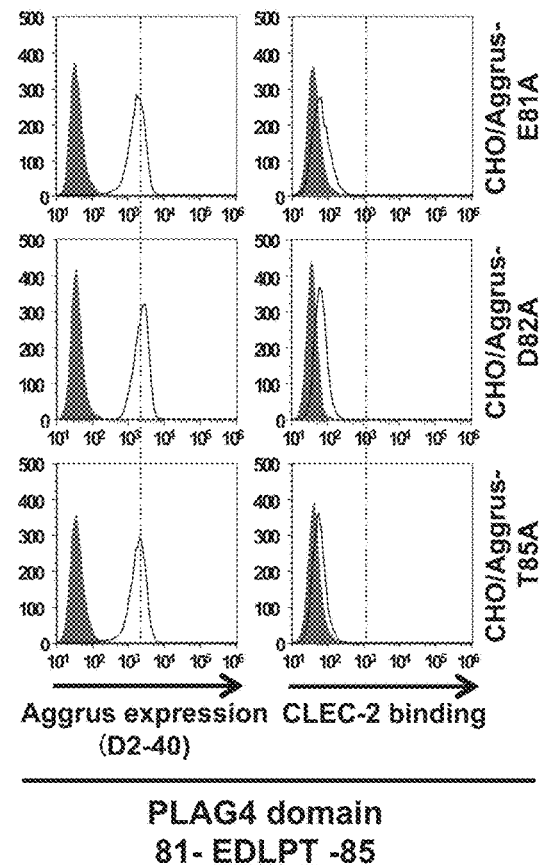
Fig. 6A
Fig. 6B
PLAG3 domain
47- EDDVVT -52
PLAG4 domain
81- EDLPT -85

71-SVNSVT GIR I EDLPT SESTV-90

ANTI-AGGRUS MONOCLONAL ANTIBODY, DOMAIN IN AGGRUS WHICH IS REQUIRED FOR BINDING TO CLEC-2, AND METHOD FOR SCREENING FOR AGGRUS-CLEC-2 BINDING INHIBITOR

TECHNICAL FIELD

The present invention relates to a region of Aggrus involved in the binding to CLEC-2, and antibodies recognizing the region. The present invention also relates to an Aggrus-CLEC-2 binding inhibitor containing a peptide comprising the region of Aggrus, or a monoclonal antibody, and a pharmaceutical composition comprising the same. The present invention further relates to a method for screening for a drug by using binding to the region as an index.

BACKGROUND ART

Cancer is a disease characterized in that cells grow disorderly. A major factor in determining the fatality rate of cancer is growth in a metastatic lesion rather than growth in a primary lesion where the cancer has initially developed. The actual 5-year survival rate of patients diagnosed with metastatic cancer is reportedly 20% or less. The prevention of cancer metastasis is a clinically great challenge.

It has been clinically accepted since a long time ago that cancer cell-dependent platelet aggregation is involved in the hematogenous metastasis of cancer. The group of the present inventor have established a highly metastatic cancer cell line exhibiting platelet aggregation-inducing activity, and identified a platelet aggregation-inducing factor, Aggrus, expressed on the cell membrane surface of the highly metastatic cancer cell line (Patent Literature 1 and Non Patent Literature 1).

The platelet aggregation-promoting factor Aggrus (also known as podoplanin, gp44, T1α) is a type-I transmembrane protein and is known to be overexpressed in various cancers including squamous cell carcinoma, mesothelioma, Kaposi sarcoma, testicular tumor, brain tumor, and bladder cancer (Non Patent Literatures 2 to 13).

Recently, C-type lectin-like receptor (CLEC-2) expressed on platelet has been identified as one of the counterpart receptors of Aggrus (Non Patent Literature 14). It is known that the binding of CLEC-2 to Aggrus expressed on tumor cells activates platelet-aggregation signals in the platelet even in the absence of plasma components to induce platelet aggregation. In other words, a substance inhibiting the binding between Aggrus and CLEC-2 is considered to inhibit platelet aggregation and inhibit cancer metastasis. Thus, the substance inhibiting the binding between Aggrus and CLEC-2 is expected to be applied to the treatment of cancer or thrombosis. In actuality, the present inventors disclose that monoclonal antibodies or low-molecular compounds against Aggrus inhibiting the interaction between Aggrus and CLEC-2 can inhibit platelet aggregation or cancer metastasis (Patent Literatures 2 and 3 and Non Patent Literature 15).

Monoclonal antibodies can specifically bind to cell surface antigens and can thereby cause immunological response to the target cells. By use of this reaction, many monoclonal antibodies are used in the treatment of cancer or the treatment of immunological disease. The monoclonal antibodies exhibit a therapeutic effect via three typical modes of action: neutralization, antibody-dependent cellular cytotoxicity (ADCC), and complement-dependent cytotoxicity (CDC).

The present inventors have previously revealed that all anti-Aggrus monoclonal antibodies P2-0 (Accession No. FERM BP-11446 deposited on Feb. 18, 2011), MS-1 (Accession No. FERM BP-11447 deposited on Dec. 28, 2011), MS-3 (Accession No. FERM BP-11448 deposited on Dec. 28, 2011), and MS-4 (Accession No. FERM BP-11449 deposited on Dec. 28, 2011) deposited with International Patent Organism Depositary National Institute of advanced Industrial Science and Technology, AIST Tsukuba Central 6, 1-1, Higashi 1-chome Tsukuba-shi, Ibaraki-ken, 305-8566, Japan, produced by established hybridomas are neutralizing antibodies that inhibit Aggrus-CLEC-2 binding, and exhibit effects of inhibiting platelet aggregation, inhibiting cancer metastasis, and inhibiting tumor growth in an ADCC activity-independent manner (Patent Literature 2).

Among these four antibodies, both the P2-0 and MS-1 antibodies having high activity of inhibiting Aggrus-CLEC-2 binding are antibodies recognizing intraregional amino acids of a PLAG domain (platelet-aggregation stimulating domain) as an epitope. The PLAG domain is an amino acid sequence having a consensus sequence EDXXVTPG (SEQ ID NO: 15) conserved across species, including humans, mice, and rats. The PLAG domain is an amino acid sequence containing three tandem repeats of the PLAG domain (PLAG1 to PLAG3) in proximal regions, and, in the case of human Aggrus, is located in a region from positions 29 to 54 of the amino acid sequence.

The PLAG domain is known to be present extracellularly and involved in platelet-aggregating activity. Results of co-crystal structure analysis on Aggrus and CLEC-2 show that glutamic acid at position 47 and aspartic acid at position 48 as well as sialic acid attached to threonine at position 52 in Aggrus binds to four arginine residues present in a region from positions 107 to 157 of CLEC-2 (Non Patent Literature 16). The P2-0 and MS-1 antibodies developed by the present inventors also recognize, as an epitope, a region from positions 45 to 49 of the amino acid sequence of Aggrus, which overlaps with the CLEC-2-binding region of Aggrus. The MS-3 and MS-4 antibodies recognize, as an epitope, a region from positions 54 to 61 of the amino acid sequence of Aggrus, which is located in proximity to the CLEC-2-binding region of Aggrus.

CITATION LIST

Patent Literature

Patent Literature 1: Japanese Patent Laid-Open No. 2004-350677
Patent Literature 2: International Publication No. WO 2012/128082
Patent Literature 3: Japanese Patent Laid-Open No. 2013-71916

Non Patent Literature

Non Patent Literature 1: Kato Y. et al., 2003, J. Biol. Chem., Vol. 278, p. 51599-51605
Non Patent Literature 2: Kato, Y. et al., 2005, Tumour. Biol. Vol. 26, p. 195-200
Non Patent Literature 3: Martin-Villar, E. et al., 2005, Int. J. Cancer, Vol. 113, p. 899-910
Non Patent Literature 4: Yuan P. et al., 2006, Cancer, Vol. 107, p. 563-569
Non Patent Literature 5: Wicki, A. et al., 2006, Cancer Cell, Vol. 9, p. 261-272

Non Patent Literature 6: Kimura, N. & Kimura, I., 2005, Pathol. Int., Vol. 55, p. 83-86
Non Patent Literature 7: Fukunaga, M., 2005, Histopathology, Vol. 46, p. 396-402
Non Patent Literature 8: Kato, Y. et al., 2004, Oncogene, Vol. 23, p. 8552-8556
Non Patent Literature 9: Mishima, K. et al., 2006, Acta Neuropathol., Vol. 111, p. 563-568
Non Patent Literature 10: Mishima, K. et al., 2006, Acta Neuropathol., Vol. 111, p. 483-488
Non Patent Literature 11: Yuan, P. et al., 2006, Cancer, Vol. 107, p. 563-569
Non Patent Literature 12: Kunita, A. et al., 2007, Am. J. Pathol., Vol. 170, p. 1337-1347
Non Patent Literature 13: Takagi, S. et al., 2014, Int. J. Cancer, Vol. 134, p. 2605-2614
Non Patent Literature 14: Suzuki-Inoue, K. et al. 2007, J. Biol. Chem., Vol. 282, p. 25993-26001
Non Patent Literature 15: Fujita N.& Takagi, S., 2012, J. Biochem., Vol. 152, p. 407-413
Non Patent Literature 16: Nagae, M. et al., 2014, Structure, Vol. 22, p. 1711-1721
Non Patent Literature 17: Morrison, S. L. et al., 1984, Proc. Natl. Acad. Sci. USA, Vol. 81, p. 6851-6855
Non Patent Literature 18: Jones, P. T. et al., 1986, Nature, Vol. 321, p. 522-525
Non Patent Literature 19: Amano, K. et al., 2008, Proc. Natl. Acad. Sci. USA, Vol. 105, p. 3232-3237
Non Patent Literature 20: Takagi, S. et al., 2013, PLoS One Vol. 8, e73609

SUMMARY OF INVENTION

Technical Problem

However, as given below, it has been revealed that even an alanine substitution mutant of aspartic acid at position 48 of Aggrus in which position is involved in the binding to CLEC-2 as a result of co-crystal structure analysis with CLEC-2, also binds to CLEC-2. As for platelet aggregation induced by the alanine substitution mutant of aspartic acid at position 48 of Aggrus, it has also been confirmed that this Aggrus mutant finally causes platelet aggregation, though the platelet aggregation-starting time is delayed.

The present inventors disclose monoclonal antibodies or low-molecular compounds against Aggrus inhibiting the interaction between Aggrus and CLEC-2 can inhibit platelet aggregation and furthermore, can inhibit cancer metastasis (Patent Literatures 2 and 3). Such monoclonal antibodies or low-molecular compounds were effective for delaying the platelet aggregation-starting time, but were unable to completely inhibit platelet aggregation induced by Aggrus. This suggests the possibility that the CLEC-2-binding site of Aggrus is also present in a region other than the known PLAG domains.

An object of the present invention is to search for a novel domain of Aggrus involved in the binding to CLEC-2 and to obtain monoclonal antibodies binding to the domain. Another object of the present invention is to provide a method for screening for a compound inhibiting cancer growth and metastasis or platelet aggregation by searching for a compound binding to the domain.

Solution to Problem

The present invention relates to monoclonal antibodies recognizing a region of Aggrus, hybridomas producing the monoclonal antibodies, a region of Aggrus necessary for the binding to CLEC-2, an Aggrus-CLEC-2 binding inhibitor, a pharmaceutical composition, a testing reagent, and a method for screening for an Aggrus-CLEC-2 binding inhibitor as given below.

(1) A monoclonal antibody binding to a region of Aggrus consisting of a sequence of at least 5 residues of the amino acid sequence represented by SEQ ID NO: 1 (GIRIEDLPT), or a fragment consisting of a functional fragment thereof.
(2) The monoclonal antibody or the fragment consisting of a functional fragment thereof according to (1), wherein the monoclonal antibody is produced by a hybridoma of deposition No. NITE P-02070 (PG4D1) or NITE P-02071 (PG4D2).
(3) The monoclonal antibody or the fragment consisting of a functional fragment thereof according to (1), wherein the monoclonal antibody is chimeric or humanized.
(4) A hybridoma of deposition No. NITE P-02070 or NITE P-02071.
(5) An Aggrus-CLEC-2 binding inhibitor comprising a monoclonal antibody or a fragment consisting of a functional fragment thereof according to any one of (1) to (3).
(6) The Aggrus-CLEC-2 binding inhibitor according to (5), further comprising at least one monoclonal antibody recognizing an epitope present in the region represented by SEQ ID NO: 2 (GAEDDVVTPGTSEDRYK), chimeric antibody thereof, humanized antibody thereof, and/or fragment consisting of a functional fragment thereof.
(7) The Aggrus-CLEC-2 binding inhibitor according to (6), wherein the monoclonal antibody recognizing the epitope present in the region of SEQ ID NO: 2 is P2-0, MS-1, MS-3, and/or MS-4.
(8) A pharmaceutical composition for inhibition of platelet aggregation, inhibition of thrombus formation, inhibition of cancer progression or metastasis, or anti-inflammation, comprising a monoclonal antibody or a fragment consisting of a functional fragment thereof according to any one of (1) to (3).
(9) The pharmaceutical composition according to (8), further comprising at least one monoclonal antibody recognizing an epitope present in the region represented by SEQ ID NO: 2 (GAEDDVVTPGTSEDRYK), chimeric antibody thereof, humanized antibody thereof, and/or fragment consisting of a functional fragment thereof.
(10) The pharmaceutical composition according to (9), wherein the monoclonal antibody recognizing the epitope present in the region of SEQ ID NO: 2 is P2-0, MS-1, MS-3, and/or MS-4.
(11) A testing reagent for detection of Aggrus expression, comprising a monoclonal antibody or a fragment consisting of a functional fragment thereof according to any one of (1) to (3).
(12) A region of Aggrus overlapping with a PLAG4 domain necessary for the binding to CLEC-2, wherein
the region is represented by SEQ ID NO: 1 (GIRIEDLPT).
(13) The region of Aggrus overlapping with a PLAG4 domain necessary for the binding to CLEC-2 according to (12), wherein
the amino acid sequence consists of the amino acid sequence represented by SEQ ID NO: 3 (RIEDL).
(14) An Aggrus-CLEC-2 binding inhibitor consisting of a peptide comprising a region according to (12) or (13).
(15) A pharmaceutical composition for inhibition of platelet aggregation, inhibition of thrombus formation, inhibition of cancer progression or metastasis, or anti-inflammation, comprising a peptide comprising a region according to (12) or (13) as an active ingredient.

(16) A method for screening for an inhibitor of the binding between CLEC-2 and Aggrus, comprising using, as an index, binding to an Aggrus epitope consisting of a sequence of at least 5 residues of the amino acid sequence represented by SEQ ID NO: 1 (GIRIEDLPT).

(17) The screening method according to (16), wherein binding to the amino acid sequence represented by SEQ ID NO: 3 (RIEDL) is used as an index.

(18) A method for screening for an inhibitor of the binding between CLEC-2 and Aggrus, comprising using, as an index, binding to the amino acid sequence represented by SEQ ID NO: 4 (EDXXTS).

Advantageous Effects of Invention

The present inventors found a novel PLAG domain necessary for the binding of Aggrus to CLEC-2, and were thereby able to obtain novel monoclonal antibodies binding to the region. The monoclonal antibodies binding to the region strongly inhibit the binding of Aggrus to CLEC-2 and are therefore expected to be effective for the treatment of cancer or thrombosis. Furthermore, an anticancer agent targeting the novel PLAG domain can also be screened for.

BRIEF DESCRIPTION OF DRAWINGS

FIG. 1A is a diagram showing results of examining the recognition sites of neutralizing antibodies using Aggrus mutants.

FIG. 1B is a diagram showing known PLAG domains in the amino acid sequence of human Aggrus (SEQ ID NO: 20).

Each of FIGS. 6A and 6B is a diagram showing the expression levels and CLEC-2 protein binding capabilities of wild-type Aggrus and Aggrus proteins harboring mutations at glutamic acid at position 81, aspartic acid at position 82, and threonine at position 85 of a PLAG4 domain (EDXXTS (SEQ ID NO: 4)).

Figure 7A:
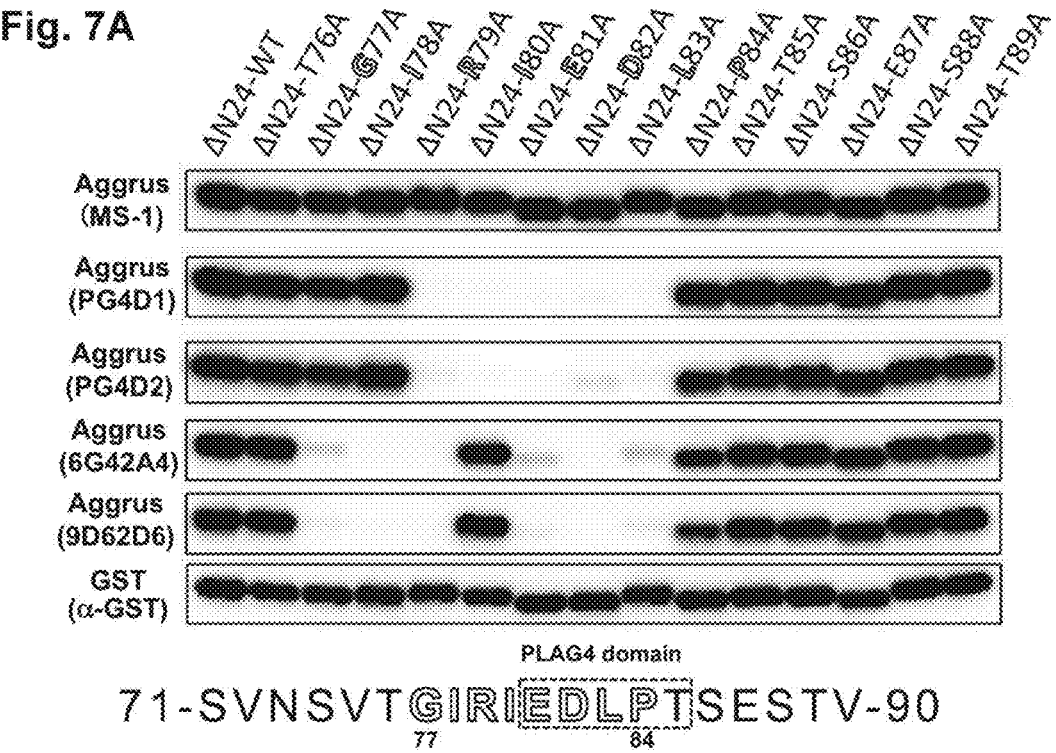

FIG. 7A is a diagram showing the epitope analysis of anti-Aggrus monoclonal antibodies.

Figure 7B:
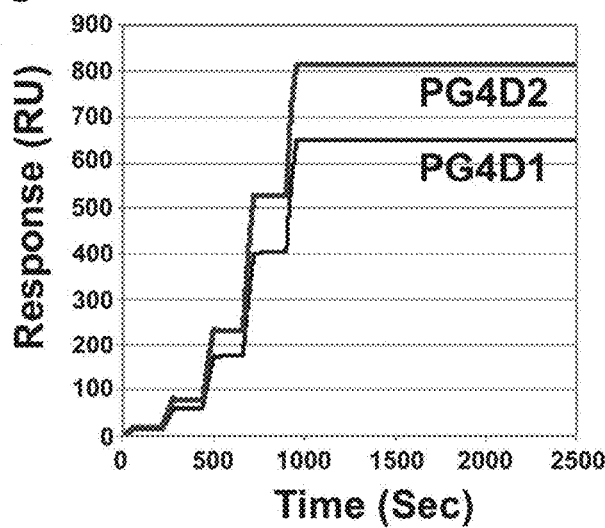

FIG. 7B is a diagram showing the reactivity of anti-Aggrus antibodies with mammalian expressed Aggrus protein.

Figure 7C:
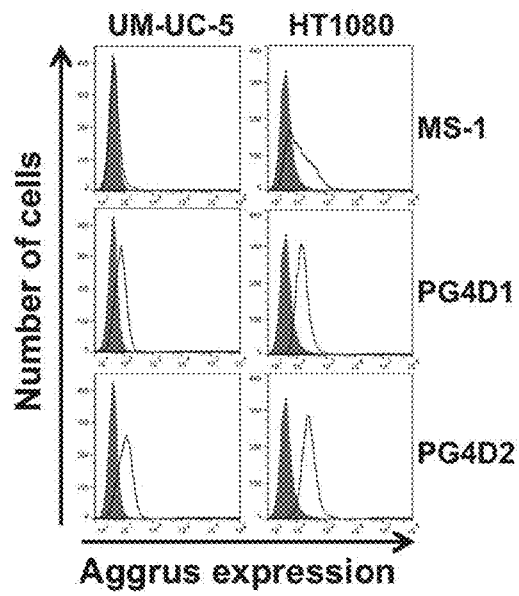

FIG. 7C is a diagram showing the reactivity of anti-Aggrus monoclonal antibodies with endogenously Aggrus-expressing cells.

Figure 8A:
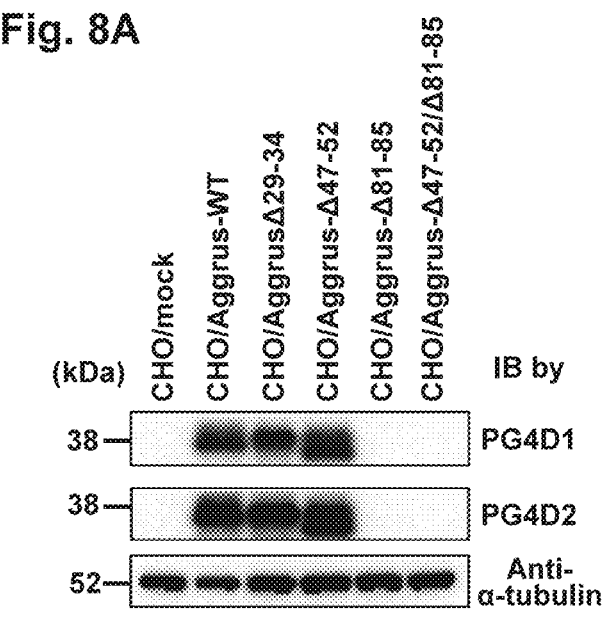
Figure 8B:
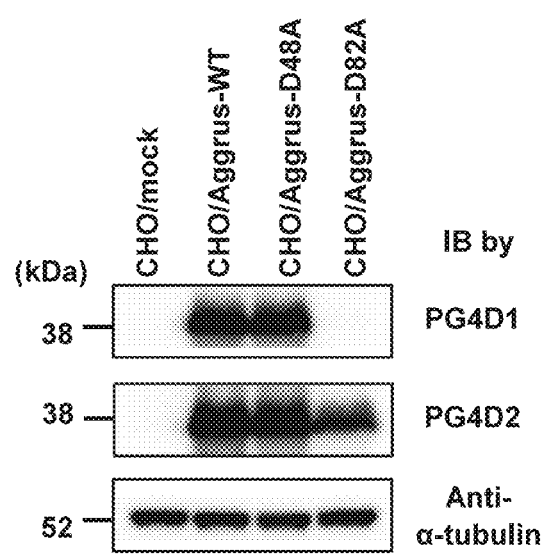

Each of FIGS. 8A and 8B is a diagram showing study on the recognition sites of the PG4D1 and PG4D2 antibodies.

Figure 8C:
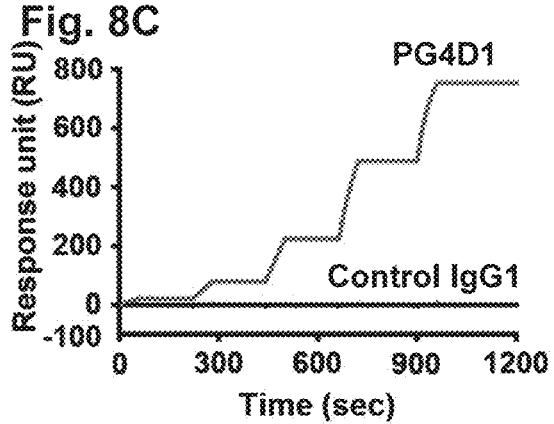

FIG. 8C is a diagram showing study on the reactivity of the PG4D1 antibody with Aggrus protein immobilized on sensor chip.

Figure 8D:
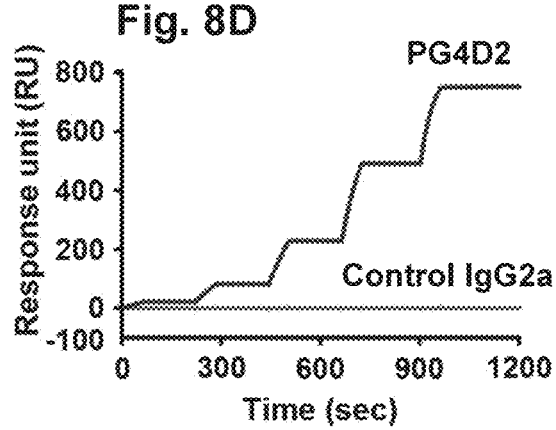

FIG. 8D is a diagram showing study on the reactivity of the PG4D2 antibody with Aggrus protein immobilized on sensor chip.

Figure 9A:
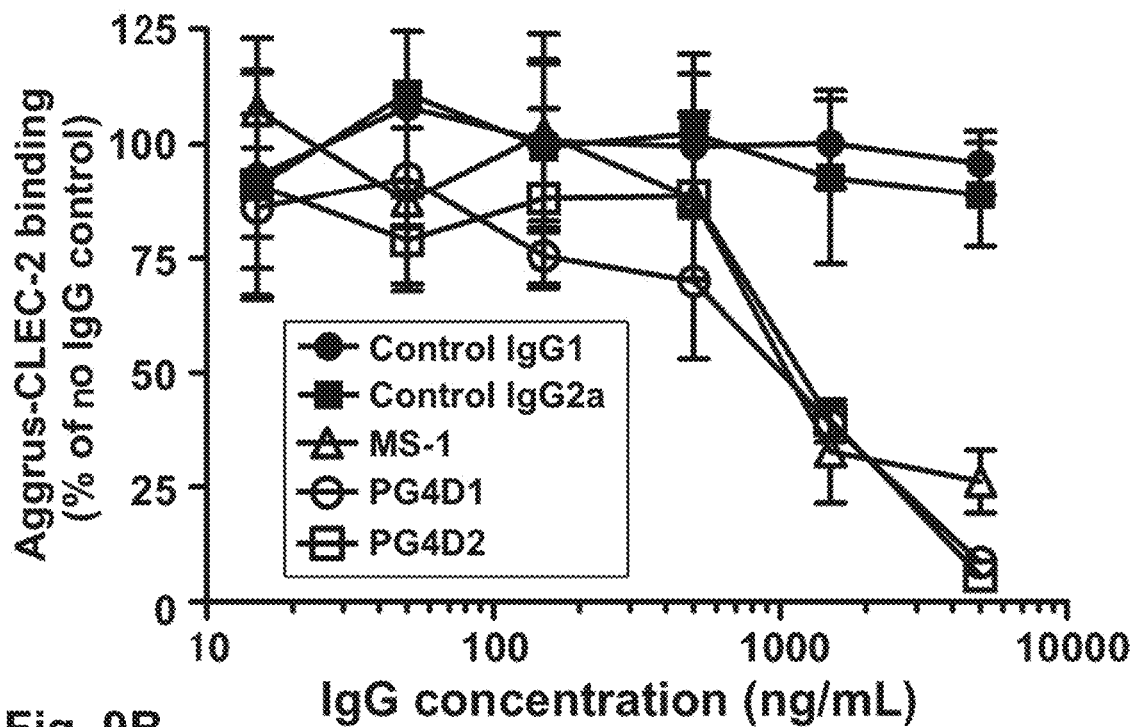
Figure 9B:
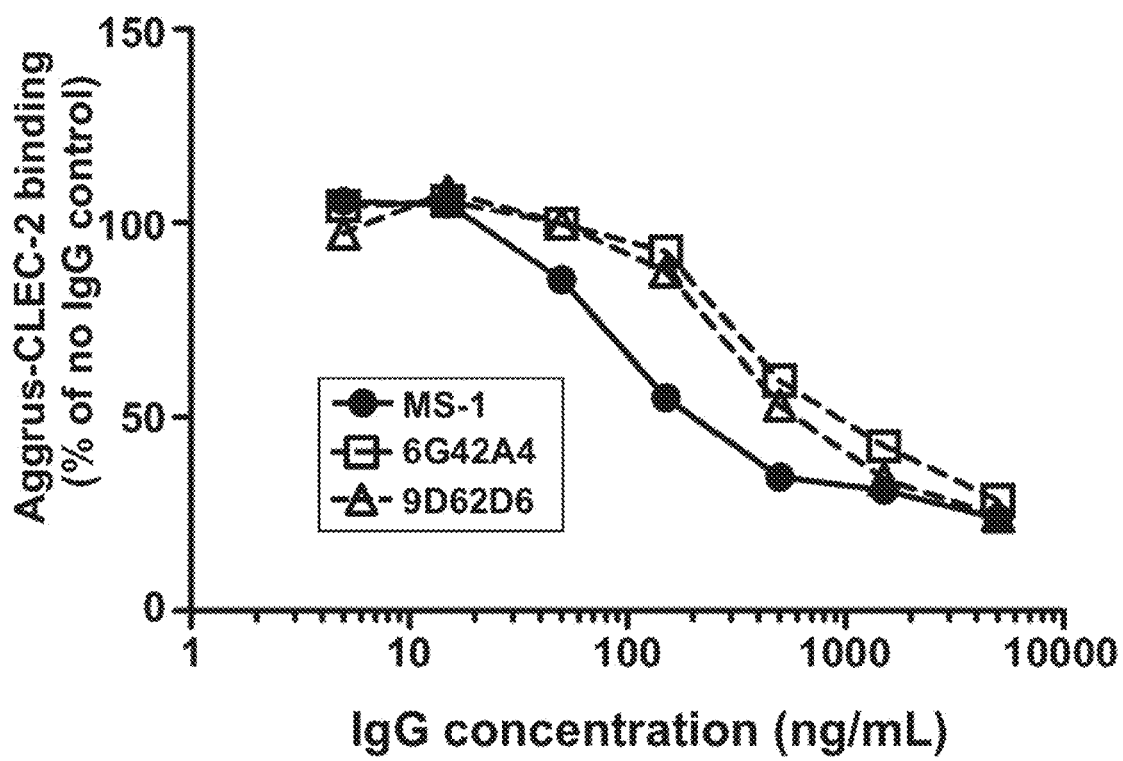

Each of FIGS. 9A and 9B is a diagram showing the inhibition of Aggrus-CLEC-2 binding by anti-Aggrus monoclonal antibodies.

Figure 10A:
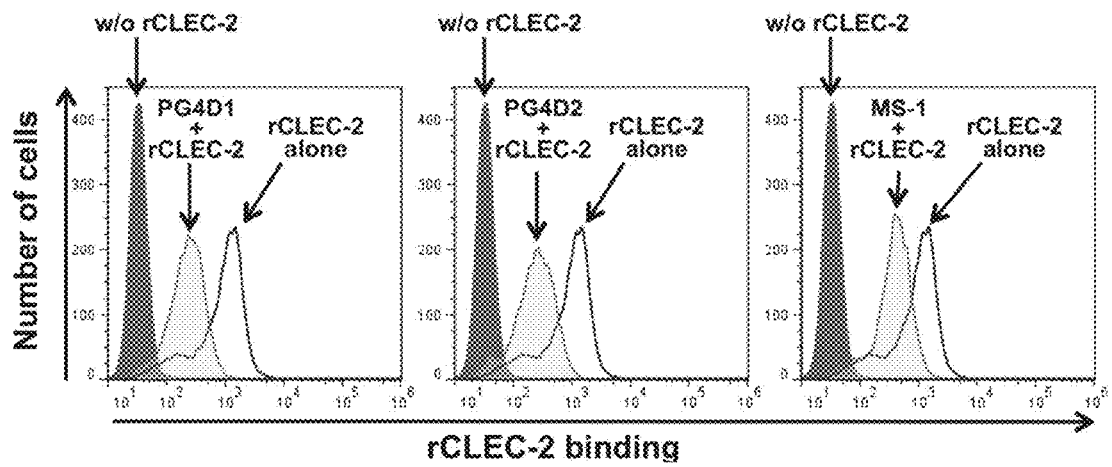

FIG. 10A is a diagram showing the inhibition of recombinant CLEC-2 binding to Aggrus-expressing cells by anti-Aggrus monoclonal antibodies.

Figure 10B:
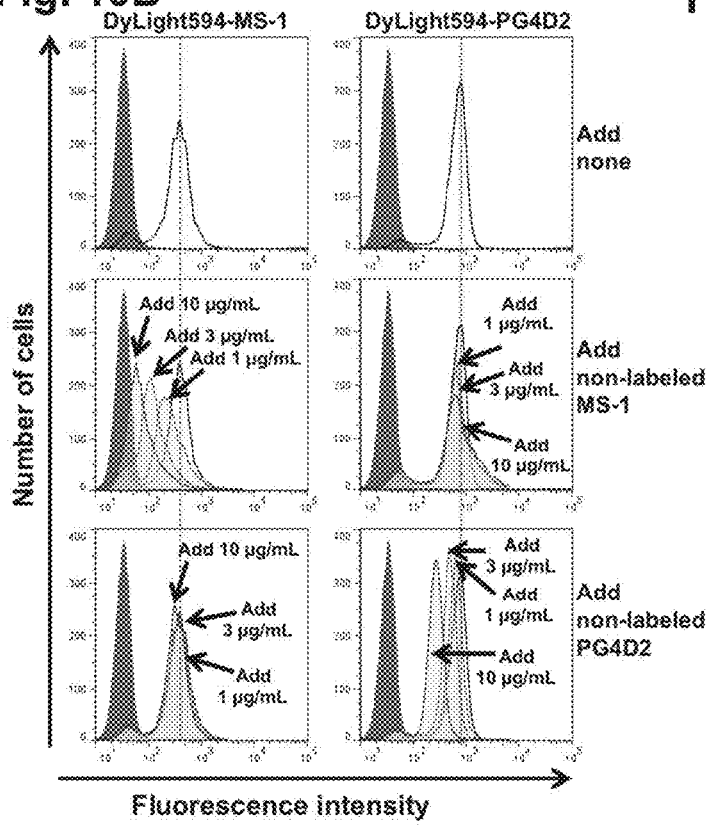

FIG. 10B is a diagram showing that antibodies respectively recognizing the PLAG3 and PLAG4 domains do not interfere with each other upon binding to Aggrus.

Figure 10C:
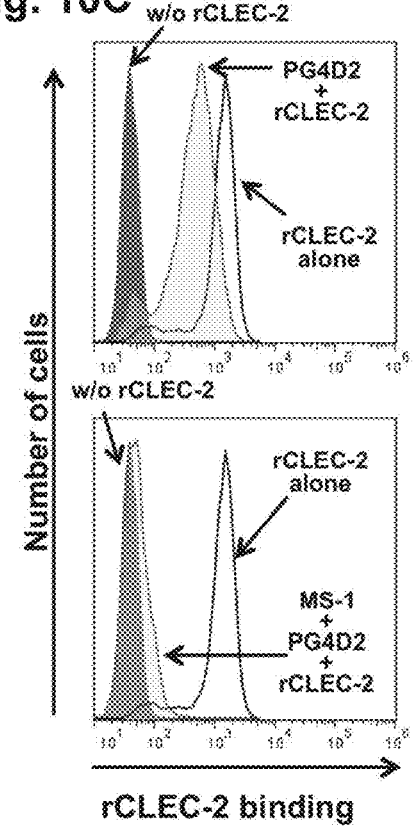

FIG. 10C is a diagram showing that the binding between Aggrus and CLEC-2 is completely inhibited by combined use of an anti-Aggrus monoclonal antibody recognizing the PLAG4 domain and an anti-Aggrus monoclonal antibody recognizing the PLAG3 domain.

Figure 11A:
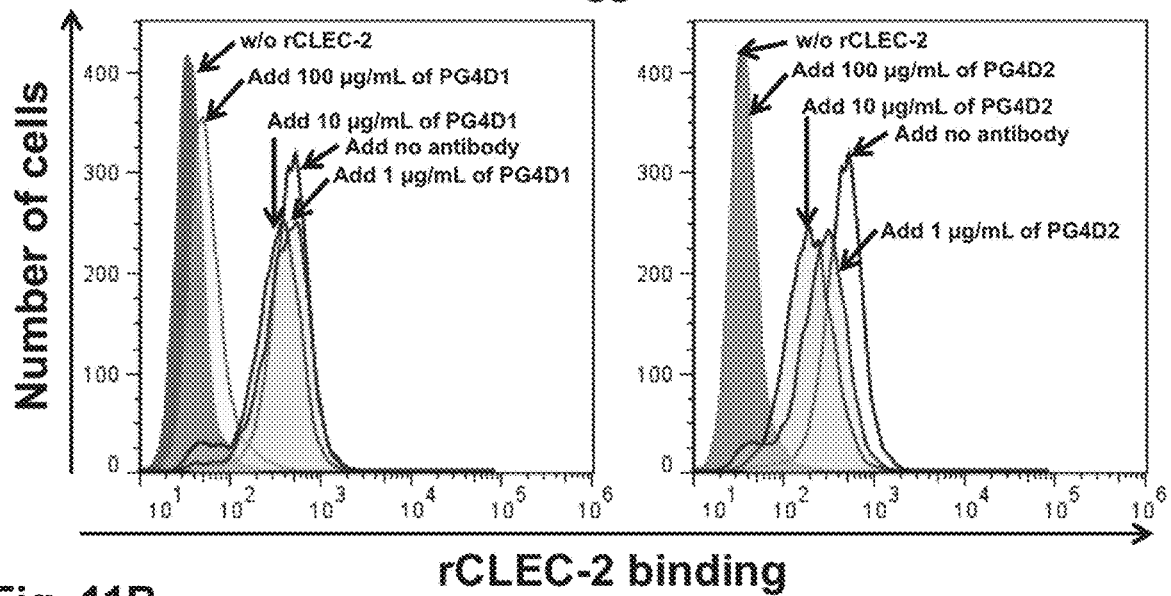

FIG. 11A is a diagram showing the inhibition of recombinant CLEC-2 binding to Aggrus by an anti-Aggrus monoclonal antibody recognizing the PLAG4 domain.

Figure 11B:
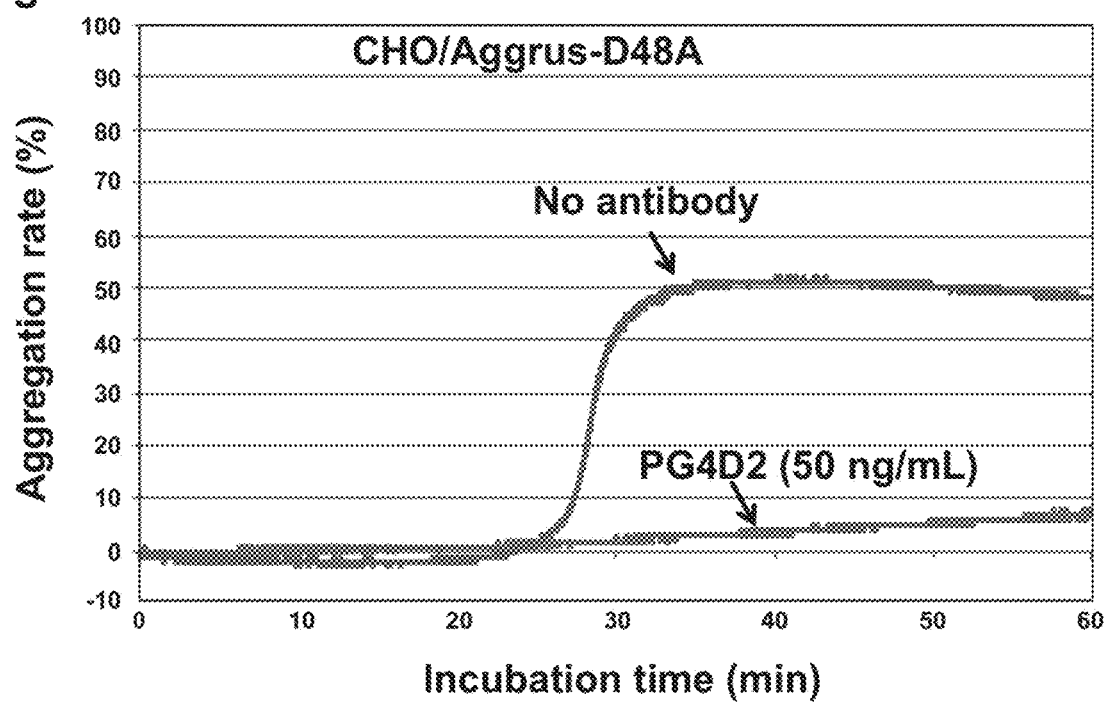

FIG. 11B is a diagram showing the inhibition of platelet aggregation by an anti-Aggrus monoclonal antibody recognizing the PLAG4 domain.

Figure 12A:
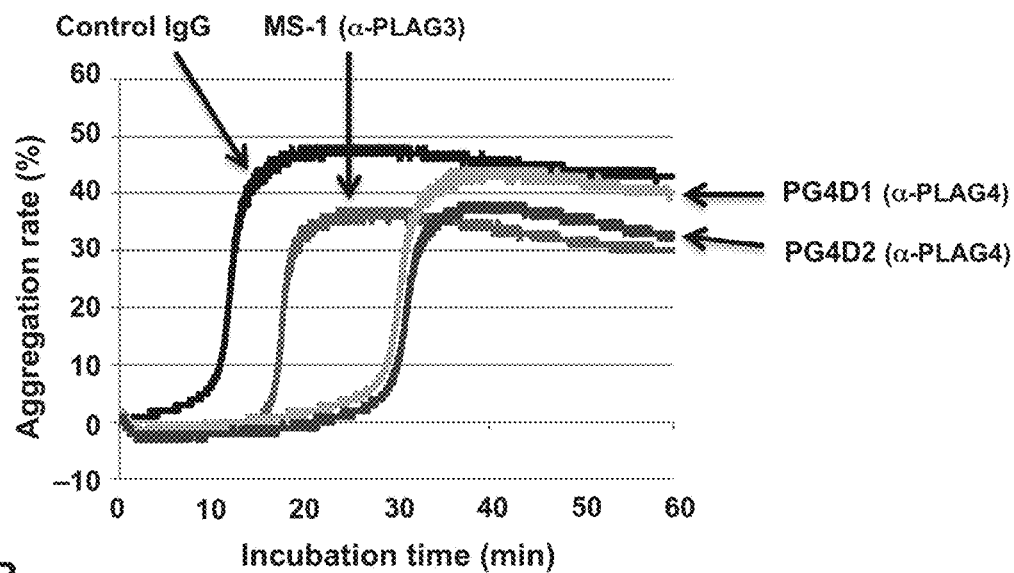

FIG. 12A is a diagram showing the inhibition of platelet aggregation by anti-Aggrus monoclonal antibodies recognizing the PLAG4 domain and an anti-Aggrus monoclonal antibody recognizing the PLAG3 domain.

Figure 12B:
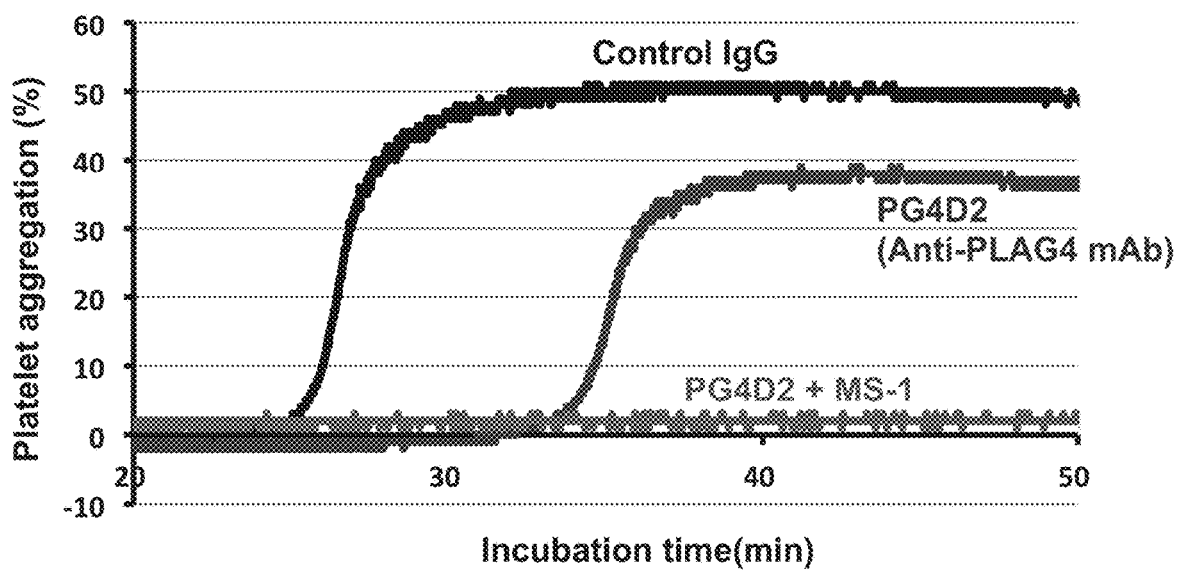

FIG. 12B is a diagram showing the inhibition of platelet aggregation induced by Aggrus-expressing cells by combined use of an anti-Aggrus monoclonal antibody recognizing the PLAG4 domain and an anti-Aggrus monoclonal antibody recognizing the PLAG3 domain.

Figure 13A:
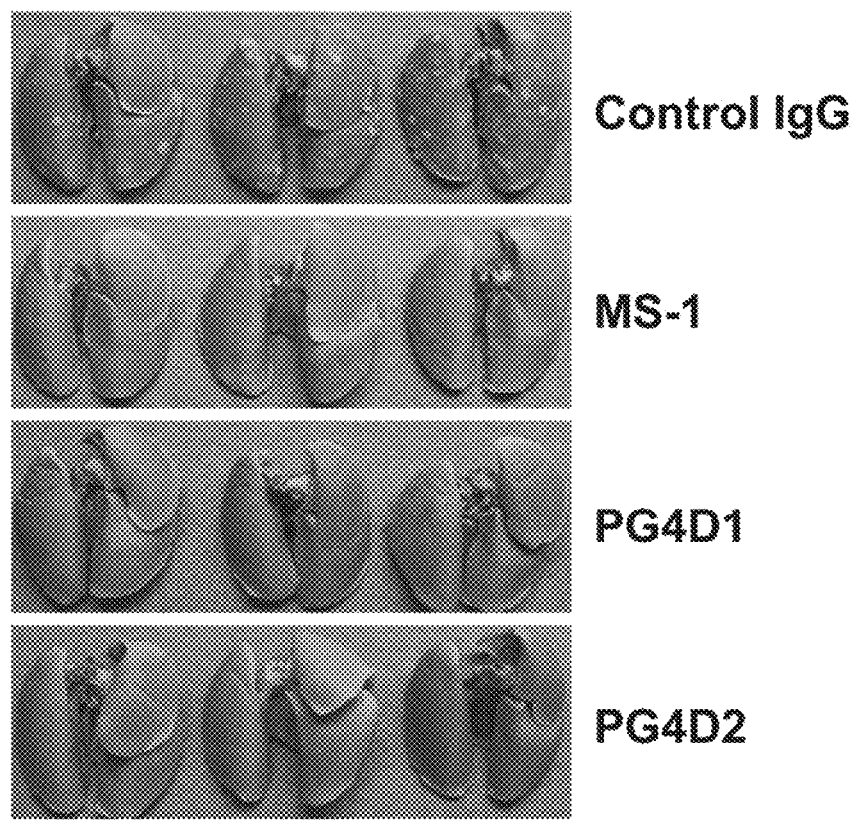
Figure 13B:
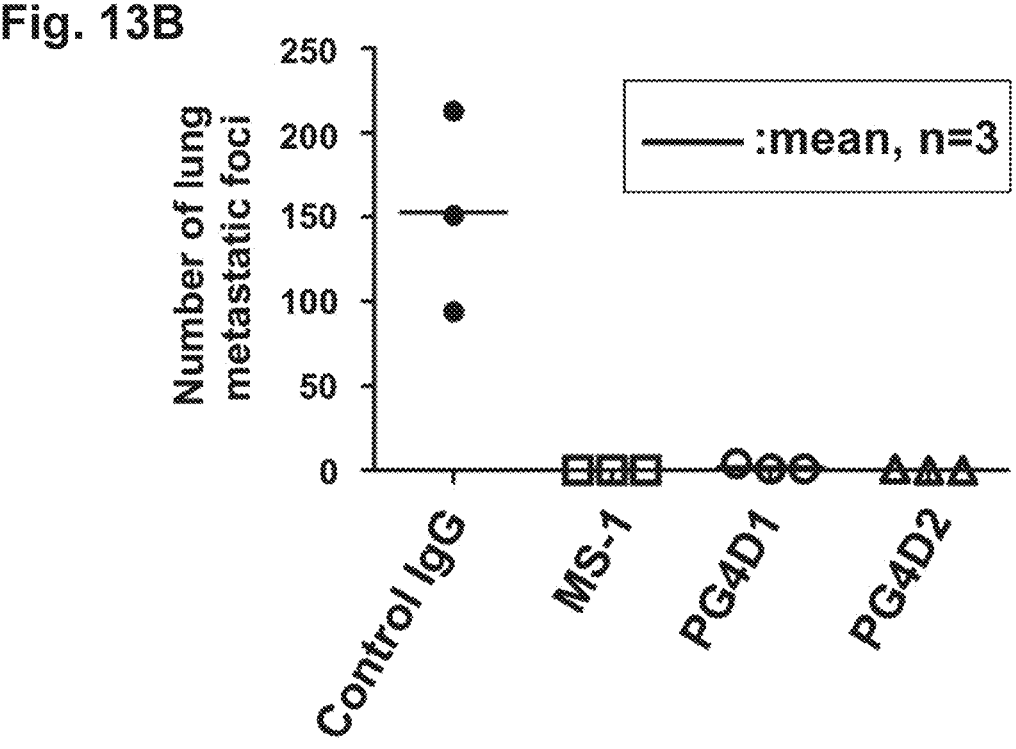

Each of FIGS. 13A and 13B is a diagram showing the inhibition of hematogenous metastasis to the lung by anti-Aggrus monoclonal antibodies recognizing the PLAG4 domain.

Figure 14A:
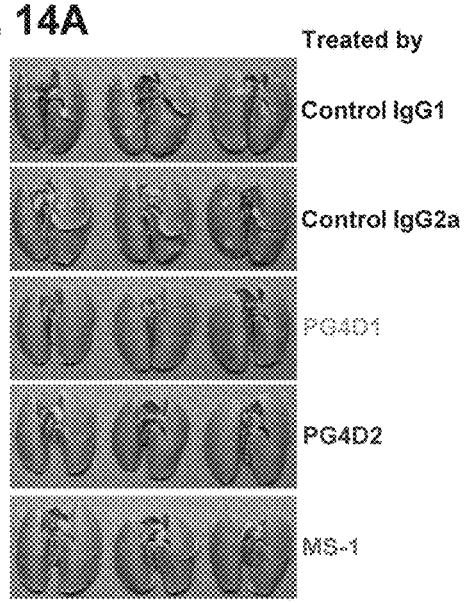
Figure 14B:
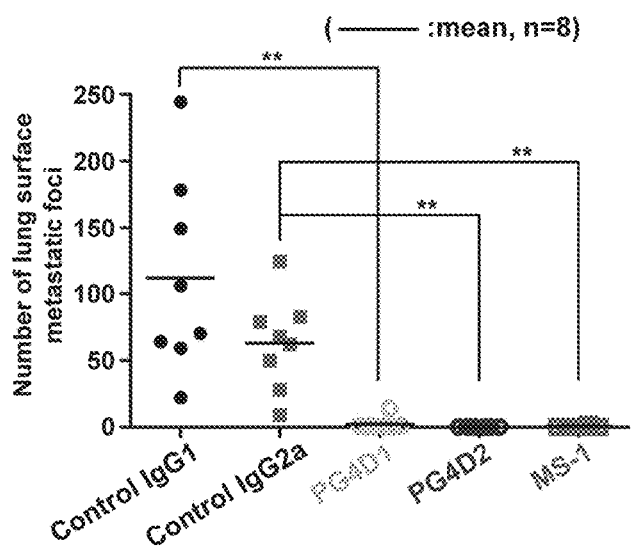

Each of FIGS. 14A and 14B is a diagram showing the inhibition of hematogenous metastasis to the lung by anti-Aggrus monoclonal antibodies recognizing the PLAG4 domain and an anti-Aggrus monoclonal antibody recognizing the PLAG3 domain.

Figure 15:
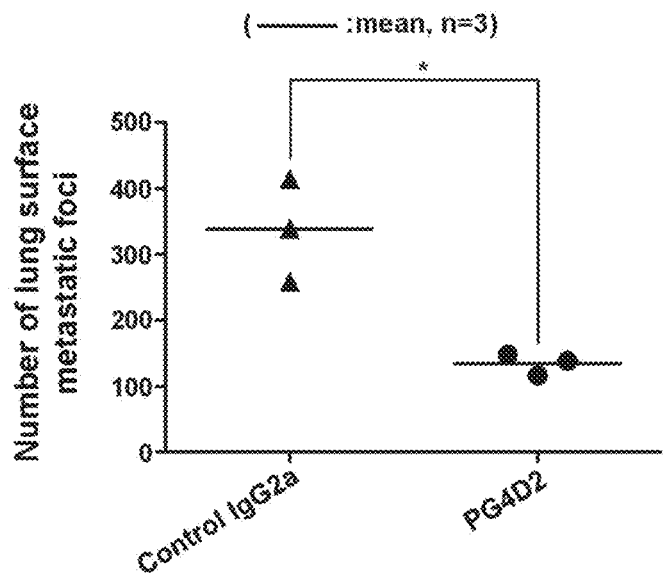

FIG. 15 is a diagram showing the inhibition of hematogenous metastasis of LC-SCC-015 cells to the lung by PG4D2 antibody.

Figure 16:
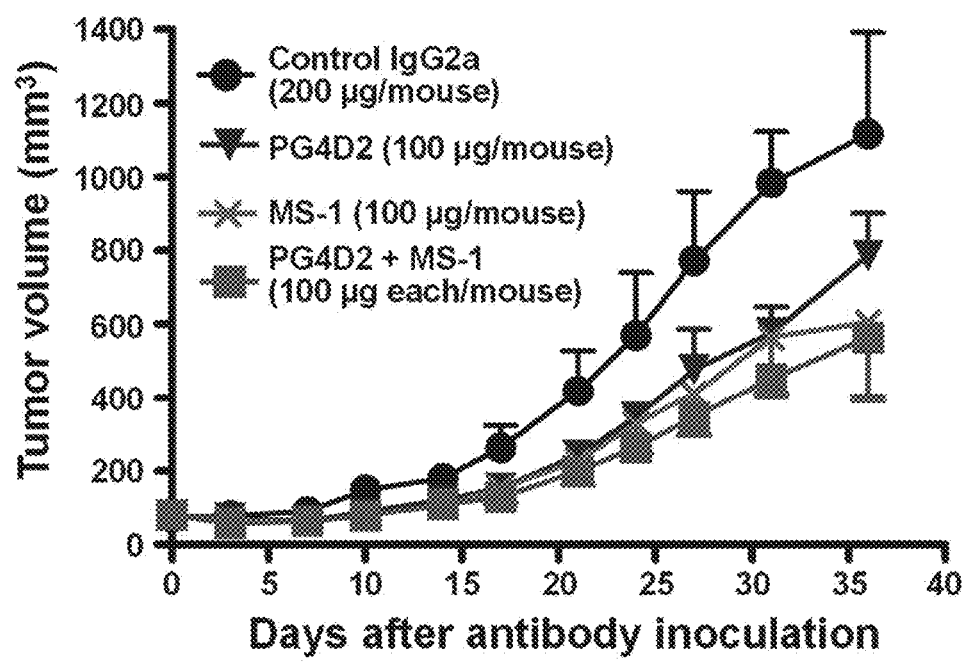

FIG. 16 is a diagram showing the inhibitory effect of an anti-Aggrus monoclonal antibody recognizing the PLAG4 domain on the tumor growth of lung squamous cell carcinoma PC-10 cells.

Figure 17A:
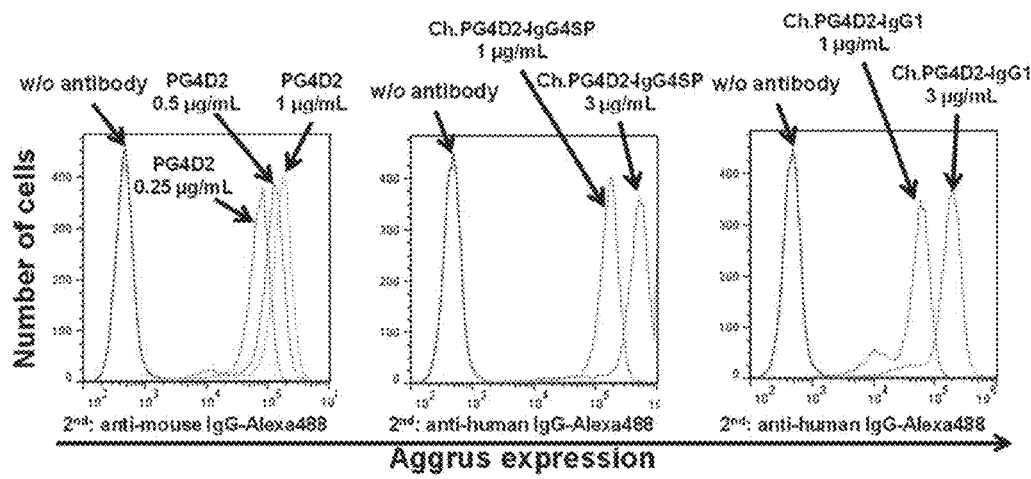

FIG. 17A is a diagram showing the binding of chimeric PG4D2 antibody to Aggrus-expressing cells.

Figure 17B:
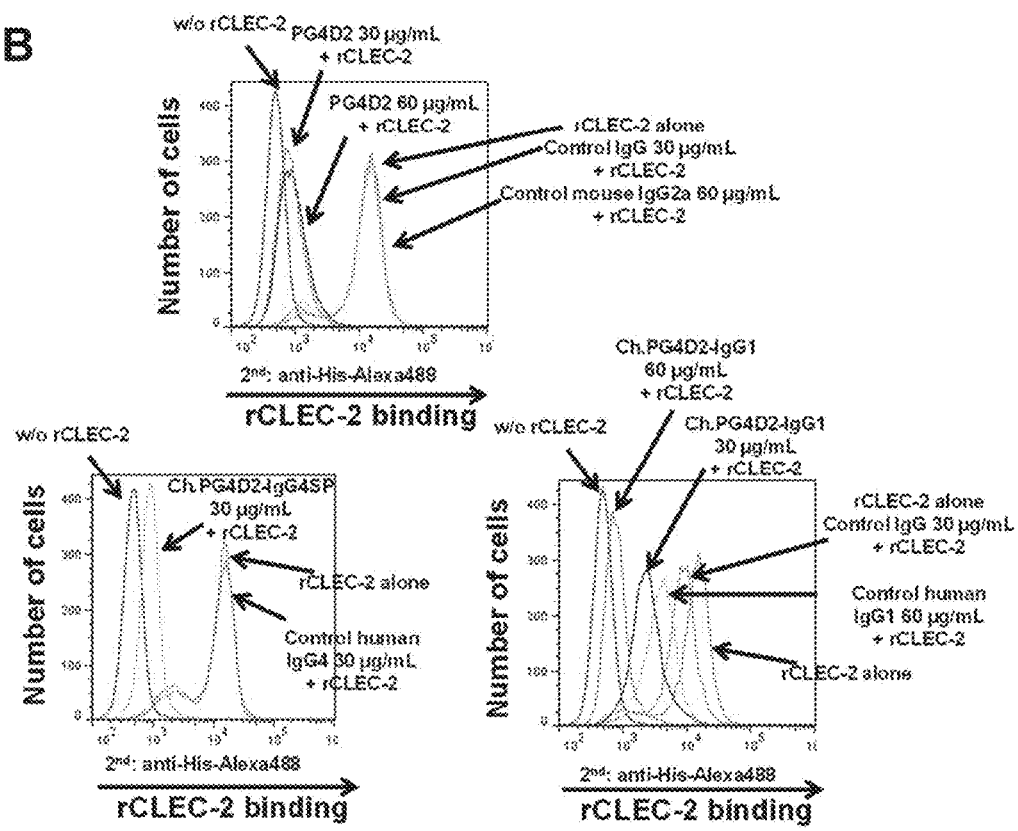

FIG. 17B is a diagram showing the inhibition of recombinant CLEC-2 binding to Aggrus by chimeric PG4D2 antibody.

Figure 18A:
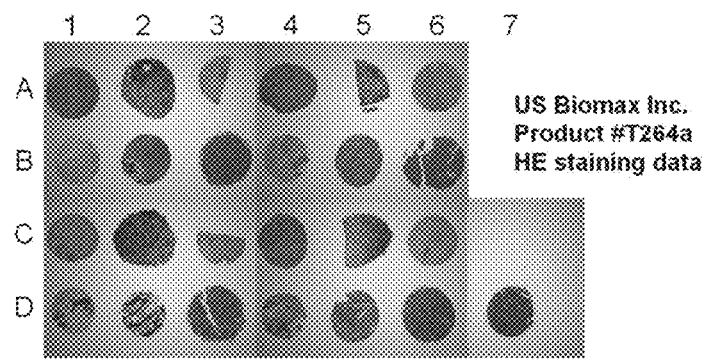

FIG. 18A show HE staining images of osteosarcoma sections.

Figure 18B:
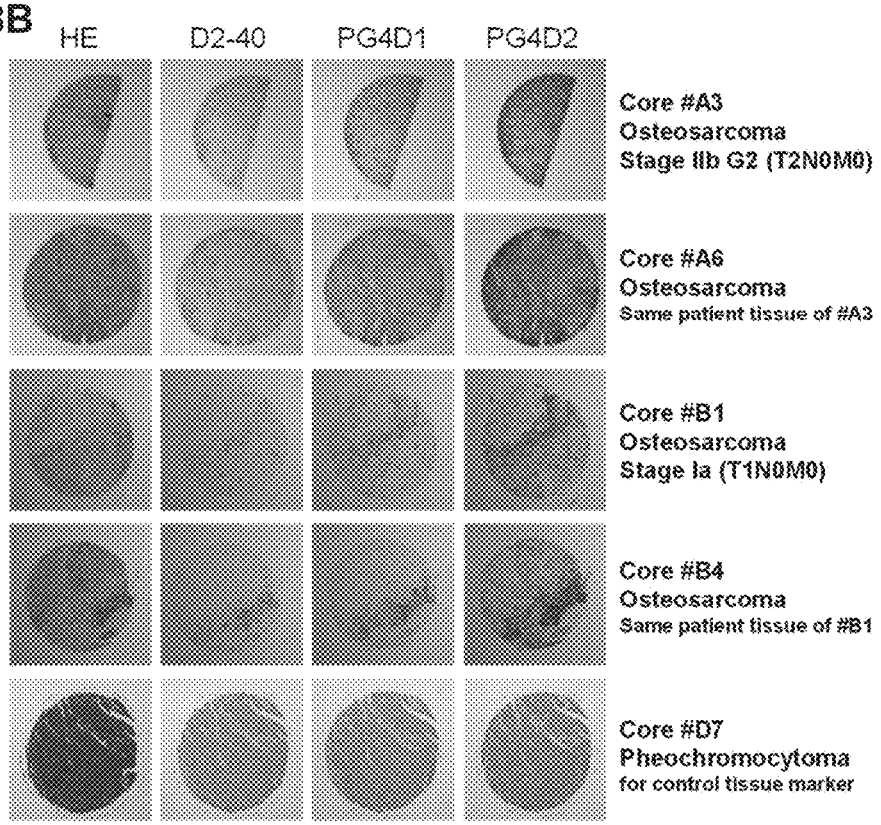

FIG. 18B is a diagram showing that the PG4D1 antibody and the PG4D2 antibody recognize osteosarcoma more sensitively than a D2-40 antibody.

DESCRIPTION OF EMBODIMENTS

The anti-Aggrus monoclonal antibody or the functional fragment of the present invention refers to an antibody recognizing, as an epitope, a region overlapping with a newly found PLAG4 domain of Aggrus, and the functional fragment refers to an antibody fragment having substantially the same antigen specificity as that of the original antibody.

Preferred examples of the monoclonal antibody against Aggrus of the present invention include monoclonal antibodies produced by hybridomas deposited on Jul. 14, 2015 under deposition Nos. NITE P-02070 and NITE P-02071, which were also deposited on Oct. 4, 2019 under Accession Nos. NITE BP-03041 and NITE BP-03042, respectively, with National Institute of Technology and Evaluation, Patent Microorganisms Depositary (NITE-NPMD (#122, 2-5-8 Kazusakamatari, Kisarazu-shi, Chiba 292-0818, Japan)). Other antibodies that possess binding specificity equivalent to these monoclonal antibodies are also preferred as the anti-Aggrus monoclonal antibody of the present invention.

In the present invention, the monoclonal antibody includes not only antibodies produced by obtained hybridomas but general antibodies whose safety is ensured when administered to humans, such as a human-type chimeric antibody (hereinafter, also referred to as a chimeric antibody) prepared by use of a gene recombination technique, or a human-type CDR (complementarity determining region)-grafted antibody (hereinafter, also referred to as a humanized antibody).

The human-type chimeric antibody refers to an antibody having variable regions of antibody (hereinafter, also referred to as V regions) derived from a non-human animal antibody and constant regions (hereinafter, also referred to as C regions) derived from a human antibody (Non Patent Literature 17). The human-type CDR-grafted antibody is an antibody in which the amino acid sequences of CDRs in the V regions of a non-human animal antibody are grafted to appropriate positions of a human antibody (Non Patent Literature 18). The chimeric antibody or the humanized antibody, when administered to humans, has fewer adverse reactions and sustains its therapeutic effect for a longer period, as compared with non-human animal antibodies. Also, the chimeric antibody or the humanized antibody can be prepared as a molecule in various forms by use of genetic recombination technique. A method known in the art can be used as a method for preparing the chimeric antibody or the humanized antibody from the monoclonal antibody.

The functional fragment of the antibody includes antibody functional fragments such as Fab, Fab', F(ab')$_2$, a single-chain antibody (scFv), a disulfide-stabilized V fragment (dsFv), and a peptide comprising CDRs. The functional fragment of the antibody can be obtained by a method known in the art such as digestion with an enzyme such as pepsin or papain.

In an alternative aspect, the present invention can provide a pharmaceutical composition for use as an Aggrus-CLEC-2 binding inhibitor, a platelet aggregation inhibitor, or an anticancer agent, comprising the monoclonal antibody or the fragment thereof. The platelet aggregation inhibitor can be used for treating thrombosis, for example, cerebral infarction or myocardial infarction. The anticancer agent can be used not only as a cancer metastasis inhibitor but for inhibiting cancer progression or inflammation caused by cancer. The pharmaceutical composition can be expected to act preferably on cancer or tumor previously confirmed to overexpress the Aggrus molecule, i.e., squamous cell carcinoma, fibrosarcoma, mesothelioma, Kaposi sarcoma, testicular tumor, brain tumor, or bladder cancer.

In the case of a peptide or antibody drug, for example, an injection which is a parenteral formulation is generally used as the type of the dosage form of the pharmaceutical composition of the present invention. Alternatively, for example, a compound obtained by screening can be administered not only as an injection but as an oral or parenteral formulation. Examples of the oral formulation include tablets, powders, pills, dusts, granules, soft or hard capsules, film-coated formulations, pellets, sublingual formulations, and pastes. Examples of the parenteral formulation can include injections as well as suppositories, percutaneous formulations, ointments, and solutions for external use. However, the pharmaceutical composition of the present invention is not limited by the dosage forms listed herein, and those skilled in the art can appropriately select the optimum dosage form according to an administration route and a recipient. In the case of using the anti-Aggrus antibody of the present invention as an active ingredient, the preparation can contain 0.1 to 99.9% by weight of the anti-Aggrus antibody.

The dose of the active ingredient in the drug can be appropriately determined as the optimum dose according to a recipient, a target organ, symptoms, and an administration method. In the case of oral administration, generally 0.1 µg to 1000 mg, preferably 1.0 µg to 100 mg, more preferably 1.0 mg to 50 mg, per day is administered to a patient. In the case of parenteral administration, the single dose differs depending on a recipient, a target organ, symptoms, an administration method, etc. For example, in the form of an injection, generally approximately 0.01 to 30 mg, preferably approximately 0.1 to 20 mg, more preferably 0.1 to 10 mg, per day is administered to a patient by intravenous injection. However, the dose can be finally determined at a physician's discretion in consideration of the age, body weight, symptoms, etc. of the patient.

It has been revealed that combined use of an antibody recognizing the PLAG4 domain and an antibody recognizing a region over PLAG2 and PLAG3 almost completely inhibits the binding between Aggrus and CLEC-2. Thus, combined use of these antibodies recognizing the two regions involved in the binding of Aggrus to CLEC-2 can be expected to produce a stronger platelet aggregation or cancer metastasis inhibitory effect.

As mentioned above, the present inventors have already obtained monoclonal antibodies recognizing, as an epitope, a region from positions 45 to 61 (SEQ ID NO: 2) of Aggrus, which is a region comprising Aggrus PLAG2 and PLAG3. Specifically, these monoclonal antibodies are P2-0 and MS-1 antibodies recognizing a region from positions 45 to 49 of Aggrus, a MS-3 antibody recognizing a region from positions 53 to 58, and a MS-4 antibody recognizing region from positions 53 to 61. The present inventors have already disclosed that a chimeric P2-0 antibody possesses a cancer metastasis inhibitory effect in an experimental system using mouse models (Patent Literature 2). In the case of clinically utilizing a monoclonal antibody recognizing this region, a chimeric or humanized antibody can be used. Use of the antibody of the present invention in combination with at least any one of these monoclonal antibodies can be expected to produce a higher effect. When these two antibodies used in combination are used as chimeric antibodies or humanized antibodies and applied to the treatment of thrombosis or cancer, a stronger effect can be expected.

The antibody of the present invention recognizing Aggrus can be used in a cancer screening. It has already been known that the expression of Aggrus is involved in the hematogenous metastasis of cancer. Thus, prognostic prediction can be conducted by detecting the expression of Aggrus in cancer tissues or cancer cells circulating in blood using the antibody of the present invention. The Aggrus expression in cancer tissues or cancer cells can be confirmed by use of an immunological assay method known in the art, such as ELISA or FACS, using the antibody of the present invention. Furthermore, a drug containing the antibody of the present invention as an active ingredient can be expected to have a therapeutic effect on cancer expressing Aggrus.

The screening method of the present invention is aimed at searching for a substance inhibiting the binding between Aggrus and CLEC-2 and providing a compound inhibiting platelet aggregation or cancer metastasis. The screening method of the present invention can be performed, for example, as follows: a compound that interacts with the newly identified amino acid sequence of Aggrus involved in the binding to CLEC-2 according to the present invention is searched for using a compound array or a compound library. For the screening using the region of Aggrus involved in the binding to CLEC-2, it is preferred to use a sequence of at least 5 residues of GIRIEDLPT (SEQ ID NO: 1) recognized by the antibody of the present invention, particularly, a region RIEDL (SEQ ID NO: 3) against which an antibody exhibiting high avidity has been obtained. Alternatively, a PLAG consensus sequence EDXXTS (SEQ ID NO: 4) of the PLAG4 domain may be used. Since the region of Aggrus involved in the binding to CLEC-2 is a short region, a synthetic peptide may be used, or a recombinant comprising the region may be expressed in *E. coli*, animal cells, or the like and used.

As discovered and reported by the present inventors, a region over the PLAG2 and PLAG3 domains (amino acids 45 to 61) of Aggrus is also involved in the interaction of Aggrus with CLEC-2 (Patent Literatures 2 and 3). Thus, an Aggrus recombinant that binds, only at the newly found CLEC-2-binding region according to the present invention, to CLEC-2 by the deletion or mutation of this site may be expressed in *E. coli*, animal cells, or the like and used.

Alternatively, this site may be masked through the reaction of wild-type Aggrus expressed in *E. coli*, animal cells, or the like with the P2-0, MS-1, MS-3, or MS-4 antibody so that the resulting Aggrus binds, only at the newly found CLEC-2-binding region according to the present invention, to CLEC-2. The peptide or the recombinant bound with the compound can be detected using the anti-Aggrus monoclonal antibody of the present invention. The method described above is given for illustrative purposes. The screening method of the present invention is not limited thereto, and any screening method known in the art can be applied thereto, as a matter of course.

Also, the region (epitope) recognized by the antibody of the present invention can be synthesized with glycosylation and administered, and can thereby be expected to competitively inhibit the binding of Aggrus to CLEC-2. Accordingly, a peptide comprising the region recognized by the antibody can be glycosylated and used as an inhibitor of the binding between Aggrus and CLEC-2. This allows the peptide itself to be used as a platelet aggregation inhibitor or a cancer metastasis inhibitor. The glycosylation can be performed by use of a method known in the art such as the attachment of a human-type sugar chain using yeast (Non Patent Literature 19).

Hereinafter, the present invention will be described in detail with reference to Examples.

Example 1

Examination of Recognition Site of Reported Neutralizing Antibody

The present inventors have already disclosed anti-Aggrus monoclonal antibodies that inhibit the binding to CLEC-2 and have a platelet aggregation inhibitory effect and a cancer metastasis inhibitory effect (Patent Literature 2 and Non Patent Literature 20). These monoclonal antibodies were antibodies recognizing a region over the PLAG2 and PLAG3 domains as an epitope.

First, the recognition sites of these neutralizing antibodies were examined. Chinese hamster ovary (CHO) cells were transfected with plasmids given below to express human Aggrus or an Aggrus mutant. The human Aggrus gene used was wild-type Aggrus cDNA (GenBank No. AB127958.1) and was amplified by PCR according to a routine method and cloned using pcDNA3 (manufactured by Life Technologies Corp.) as a vector.

The following constructs were used in the study on the recognition sites of the neutralizing antibodies. An empty pcDNA3 vector (mock), a plasmid containing wild-type human Aggrus cDNA (Aggrus-WT), a plasmid containing Aggrus cDNA encoding a mutant containing alanine replaced for glycine at position 45 (Aggrus-G45A), a plasmid containing Aggrus cDNA encoding a mutant containing alanine replaced for aspartic acid at position 48 (Aggrus-D48A), and a plasmid containing Aggrus cDNA encoding a mutant containing alanine replaced for aspartic acid at position 49 (Aggrus-D49A) were constructed, and CHO cells were transfected with each plasmid to stably express the protein. Hereinafter, the CHO cells transfected with these plasmids are referred to as CHO/mock, CHO/Aggrus-WT, CHO/Aggrus-G45A, CHO/Aggrus-D48A, CHO/Aggrus-D49A, respectively.

A cell lysate was prepared from each cell and subjected to Western blot analysis using four anti-Aggrus monoclonal antibodies D2-40, MS-1, P2-0, and NZ-1. The D2-40 antibody (manufactured by AbD Serotec) is a mouse monoclonal antibody lacking Aggrus-neutralizing activity, and the MS-1 antibody and the P2-0 antibody are mouse monoclonal antibodies having neutralizing activity, which have been developed by the present inventors. The NZ-1 antibody (manufactured by AngioBio) is a rat monoclonal antibody having Aggrus-neutralizing activity. The results are shown in FIG. 1A.

The D2-40 antibody lacking Aggrus-neutralizing activity recognizes all the wild-type and one-amino acid-substituted Aggrus proteins in the transfectants. Specifically, signals were observed in the cells other than CHO/mock. Also, the wild-type Aggrus and the Aggrus mutants were confirmed to exhibit almost equal protein expression levels. As is also evident from the results of Western blot analysis (FIG. 1A) using an antibody recognizing α-tubulin, the protein levels in the cell lysates were the same.

The MS-1 antibody and the P2-0 antibody recognized the wild-type Aggrus, but weakly recognized the one-amino acid-substituted Aggrus proteins Aggrus-G45A, Aggrus-D48A, and Aggrus-D49A, demonstrating that these amino acid sites are essential for antibody recognition. Particularly, both the P2-0 antibody and the MS-1 antibody cannot recognize Aggrus-D48A harboring the substitution of aspartic acid at position 48 by alanine. This suggested that the aspartic acid at position 48 in the PLAG domain is important for recognition by the antibodies.

The rat monoclonal antibody NZ-1 antibody having Aggrus-neutralizing activity also weakly recognized the one-amino acid-substituted Aggrus proteins. This suggested that the mutated region from positions 45 to 49 of Aggrus, i.e., the site over PLAG2 and PLAG3 (see FIG. 1B), is important for exerting neutralizing activity.

Example 2

Study on site of Aggrus involved in interaction with CLEC-2 and induction of platelet aggregation (1) Study on Role of Aspartic Acid at Position 48 of Aggrus in CLEC-2 Binding CHO cells were transfected with plasmids containing human Aggrus cDNA or mutant cDNA thereof, and the role of aspartic acid at position 48 was studied. The wild-type Aggrus-expressing cell line CHO/Aggrus-WT and the mutant-expressing CHO cell line CHO/Aggrus-D48A prepared as described above, CHO/Aggrus-D48E harboring the substitution of aspartic acid at position 48 by glutamic acid, and CHO/Aggrus-D48N harboring the substitution of aspartic acid at position 48 by asparagine were used and studied for their reactivity with recombinant CLEC-2 by FACS.

First, Aggrus expression levels in the transfectants CHO/Aggrus-WT, CHO/Aggrus-D48E, CHO/Aggrus-D48N, and CHO/Aggrus-D48A were studied. Specifically, these transfectants were each recovered from a culture vessel, washed with PBS, and then adjusted to a cell density of $1.5 \times 10^5$ cells/ml. The D2-40 antibody was added thereto and reacted on ice for 30 minutes. Then, the cells were washed with PBS, and an Alexa 488-labeled anti-mouse IgG antibody (manufactured by Life Technologies Corp.) was added thereto as a secondary antibody and further reacted on ice for 30 minutes. Finally, the cells were washed with PBS three times, followed by analysis using Cytomics FC500 (manufactured by Beckman Coulter, Inc.) (left panels of FIG. 2A, open areas). As controls, a control mouse antibody (manufactured by Sigma-Aldrich Co. LLC) is used instead of the D2-40 antibody with each cell and performing the same operation as above are shown (left panels of FIG. 2A, closed areas).

The reactivity with CLEC-2 was studied as follows: the transfectants were each adjusted to a cell density of $1.5 \times 10^5$ cells/ml in the same way as above. A $(His)_{10}$-tagged recombinant CLEC-2 protein (rCLEC-2; manufactured by R&D Systems, Inc.) was added thereto and reacted on ice for 30 minutes. After washing with PBS, a fluorescent-labeled secondary antibody (manufactured by Qiagen Inc.) recognizing the His tag was added thereto and further reacted on ice for 30 minutes. The $(His)_{10}$-tagged recombinant CLEC-2 protein was purified from mammalian cells and modified with a sugar chain. The cells were washed with PBS three times, followed by analysis using Cytomics FC500 in the same way as above (right panels of FIG. 2A, open areas). Results of adding PBS alone instead of the $(His)_{10}$-tagged recombinant CLEC-2 protein and performing the same operation as above are shown as controls (right panels of FIG. 2A, closed areas).

Figure 2A:
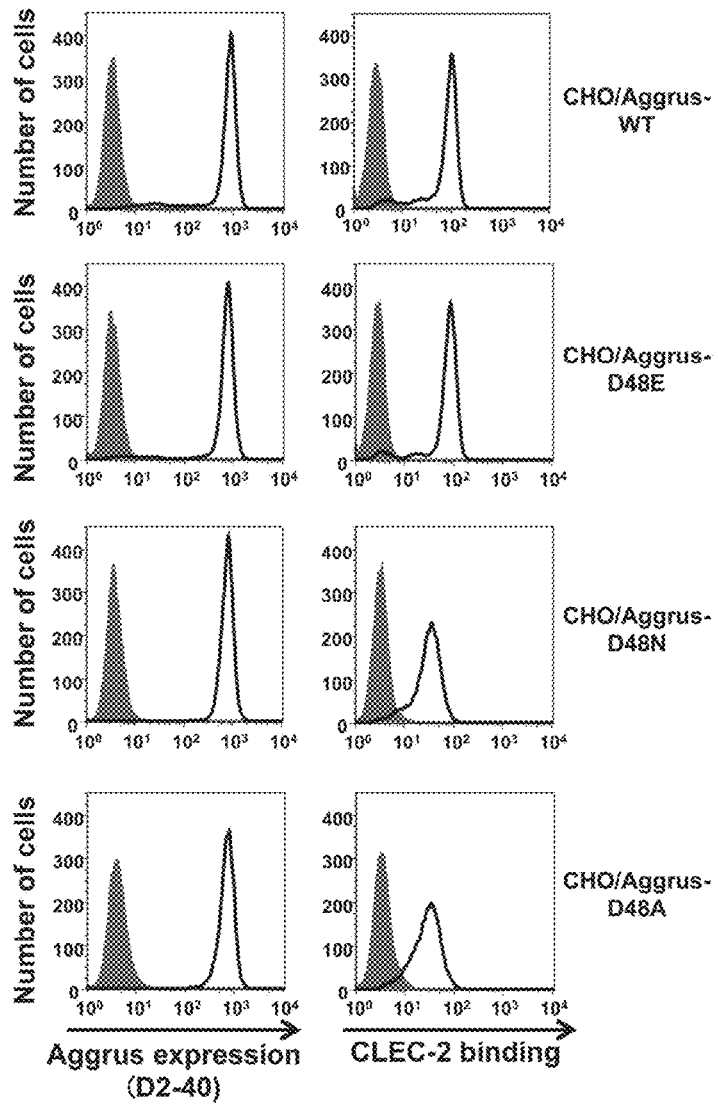
FIG. 2A is a diagram showing the expression levels and CLEC-2 protein binding capabilities of wild-type (WT) Aggrus and Aggrus mutant proteins in transfected CHO cells.

The expression of Aggrus and the Aggrus mutant proteins is shown in the left panels of FIG. 2A, and the binding to CLEC-2 is shown in the right panels of FIG. 2A. The open areas of the left panels of FIG. 2A depict the results of staining the wild-type Aggrus or the Aggrus mutants with the D2-40 antibody. The closed areas depict the results obtained using the control mouse antibody. Fluorescence intensity was almost the same among the peak positions of the open areas of the left panels of FIG. 2A, confirming that the expression levels of the Aggrus proteins on the cell surface of these transfectants are almost equal.

The right panels of FIG. 2A show analysis on whether the recombinant CLEC-2 would bind to the cells expressing the wild-type or one-amino acid-substituted Aggrus. As mentioned above, the open areas depict the results of detecting the recombinant CLEC-2 bound with the wild-type Aggrus or the Aggrus mutants expressed on CHO cell surface using the anti-His antibody. The closed areas depict the control results obtained by adding PBS alone instead of the CLEC-2 protein.

CLEC-2 binds to the D48E mutant harboring the substitution of aspartic acid at position 48 by glutamic acid, which is also an acidic amino acid (CHO/Aggrus-D48E), similarly to the wild type (CHO/Aggrus-WT). However, reduction in the binding intensity of CLEC-2 was observed in the D48N (CHO/Aggrus-D48N) or D48A (CHO/Aggrus-D48A) mutant harboring the substitution by a neutral amino acid. However, CLEC-2 was found to bind to all the mutants to some extent without completely losing the binding.

(2) Study on Role of Aspartic Acid at Position 48 of Aggrus in Platelet Aggregation As mentioned above, CLEC-2 is a receptor on platelet binding to Aggrus. Aggrus binds to CLEC-2 on platelet to thereby transduce platelet aggregation-inducing signals. The D48A mutant (CHO/Aggrus-D48A) more weakly binding to CLEC-2 was presumed to have weaker platelet aggregation-inducting activity. Therefore, this was confirmed by a platelet aggregation test. Specifically, analysis was conducted using MCM HEMA TRACER 313M (manufactured by MC Medical, Inc.). This analysis method is an in vitro platelet aggregation analysis method by the monitoring of light transmittance using washed mouse platelet.

Figure 2B:
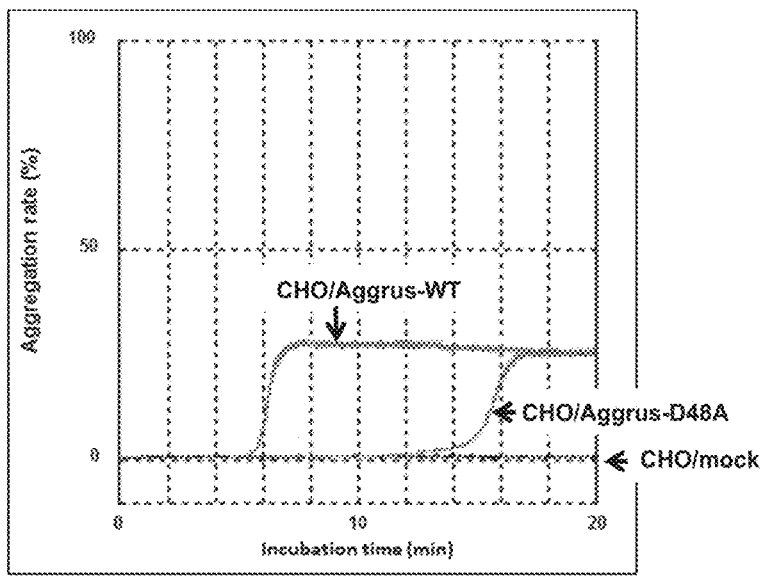
FIG. 2B is a diagram showing the effect of an amino acid mutation at position 48 (D48A) on platelet aggregation.

As shown in FIG. 2B, no activity of inducing platelet aggregation was observed in the CHO/mock cells, whereas aggregation was started approximately 6 minutes after mixing of the platelet with CHO/Aggrus-WT expressing the wild-type Aggrus. On the other hand, when CHO/Aggrus-D48A having weakened binding intensity to CLEC-2 was mixed with the platelet, aggregation was observed only from approximately 14 minutes later. Thus, the start of platelet aggregation was delayed by approximately 8 minutes. This result supports the results of FIG. 2A showing the weakened binding intensity to CLEC-2 and also suggests the possibility that: a site other than the previously identified PLAG3 domain is involved in the binding to CLEC-2; and platelet aggregation is induced by binding to CLEC-2 via the site.

Example 3

Finding of novel PLAG4 domain involved in binding to CLEC-2

Figures 3A, 3B:
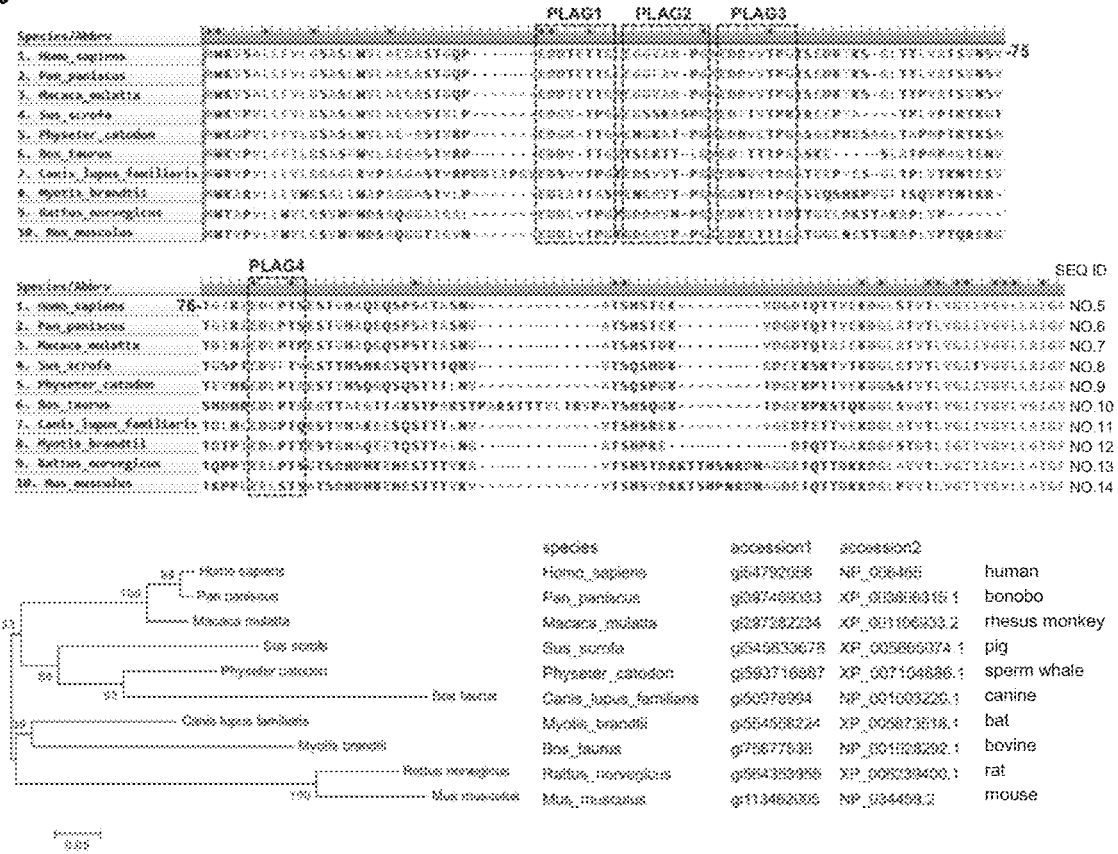
FIG. 3A is a diagram showing the homology of mammalian Aggrus amino acid sequences (SEQ ID NOs: 5-14).
FIG. 3B is a diagram showing the consensus sequence of the PLAG domains (SEQ ID NOs: 15-19).

The homology of the amino acid sequences of human (*Homo sapiens*, SEQ ID NO: 5), bonobo (*Pan paniscus*, SEQ ID NO: 6), rhesus monkey (*Macaca mulatta*, SEQ ID NO: 7), pig (*Sus scrofa*, SEQ ID NO: 8), sperm whale (*Physeter catodon*, SEQ ID NO: 9), bovine (*Bos Laurus*, SEQ ID NO: 10), canine (*Canis lupus familiaris*, SEQ ID NO: 11), bat (*Myotis brandtii*, SEQ ID NO: 12), rat (*Rattus norvegicus*, SEQ ID NO: 13), and mouse (*Mus musculus*, SEQ ID NO: 14) Aggrus proteins was studied from a mammalian phylogenetic tree (lower panel of FIG. 3A).

FIG. 3A shows the alignment of highly homologous regions of the Aggrus proteins of these animals. The sequences of the Aggrus proteins of the animals are based on the sequences of GenBank accession Nos. shown beneath FIG. 3A. As a result, a PLAG4 domain highly conserved in mammals, which is analogous to the previously reported PLAG domains 1 to 3, was found (FIG. 3A). FIG. 3B shows the consensus sequence (SEQ ID NO: 15) of the PLAG domain and the sequences of PLAG1 to PLAG4 (SEQ ID NOs: 16 to 19). A highly conserved ED sequence of glutamic acid followed by aspartic acid, reportedly involved in the binding to CLEC-2, and threonine T serving as a glycosylation site were conserved in human PLAG4. However, the number of amino acids between the ED sequence and T was found to be 2 amino acids, not previously identified 3 amino acids, in the PLAG4 domain.

Example 4

Study on role of novel PLAG4 domain in interaction with CLEC-2 and ability to induce platelet aggregation (1) Study on Expression Level of Established Aggrus Mutant CHO cells were transfected with genes of PLAG4 mutants harboring an amino acid mutation in the PLAG4 domain presumed to be a novel PLAG domain. Specifically, CHO cells were transfected with a plasmid prepared by integrating a pcDNA3 vector with human Aggrus cDNA encoding a mutant containing alanine replaced for aspartic acid at position 82, which is an amino acid in the PLAG4 region (Aggrus-D82A) or a plasmid prepared by integrating a pcDNA3 vector with human Aggrus cDNA encoding a mutant containing alanine replaced both for aspartic acid at position 48 and for aspartic acid at position 82 (Aggrus-D48A/D82A), to stably express the protein. Hereinafter, the CHO cells transfected with these plasmids are referred to as CHO/Aggrus-D82A and CHO/Aggrus-D48A/D82A, respectively.

Figure 4A:
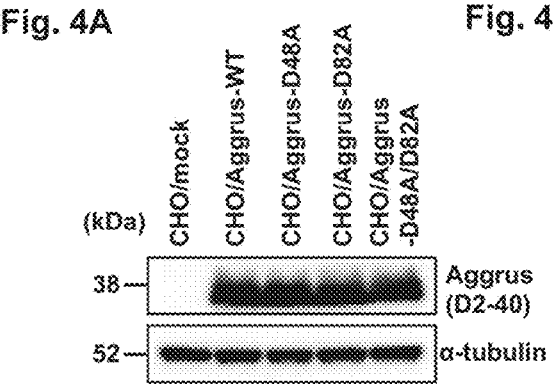
FIG. 4A is a diagram showing the levels of protein expression of Aggrus mutants.

A cell lysate was prepared from each of the CHO/mock, CHO/Aggrus-WT, CHO/Aggrus-D48A, CHO/Aggrus-D82A, and CHO/Aggrus-D48A/D82A cell lines. Each cell lysate was used in Western blot analysis using the D2-40 antibody. As a result, the expression of the wild-type and mutant Aggrus proteins in the transfectants was observed in the cells other than CHO/mock while their expression levels were confirmed to be almost equal (FIG. 4A).

(2) Study on Roles of PLAG3 and PLAG4 in Binding to CLEC-2

Figure 4B:
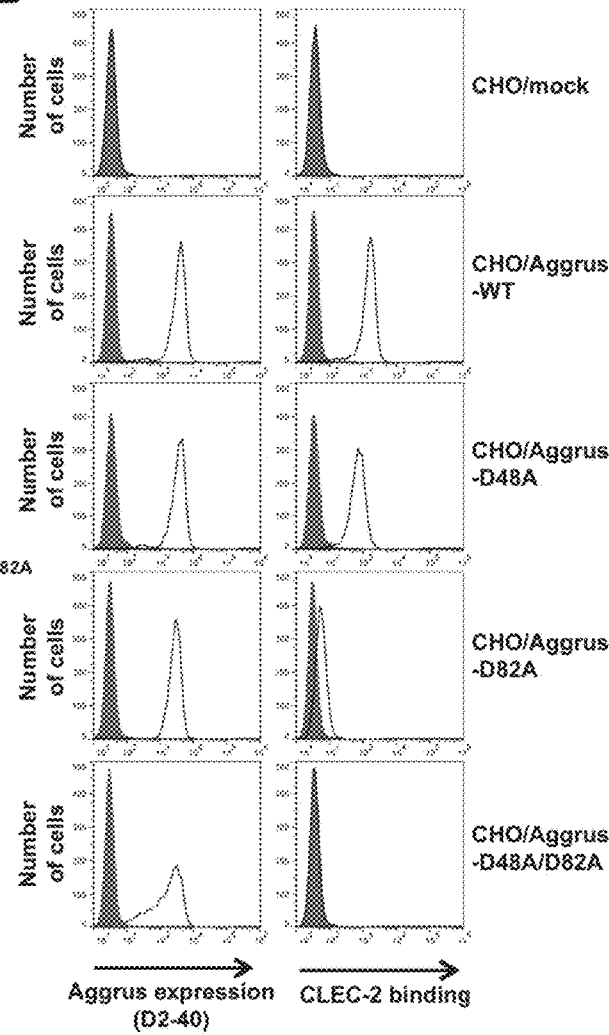
FIG. 4B is a diagram showing the expression levels and CLEC-2 protein binding capabilities of wild-type Aggrus and Aggrus mutant proteins in transfected CHO cells.

These CHO lines stably expressing the genes were used in FACS in the same way as in Example 2 to confirm Aggrus expression levels and reactivity to recombinant CLEC-2. In the left panels of FIG. 4B, the open areas depict the results of staining the wild-type Aggrus or the Aggrus mutants through reaction with the D2-40 antibody, and the closed areas depict the results of reacting a control mouse antibody (manufactured by Sigma-Aldrich Co. LLC) instead of the D2-40 antibody, as in FIG. 2A. As shown in FIG. 4B (left panels), the expression levels of the Aggrus proteins on the cell membranes of these transfectants were confirmed to be almost equal, also because fluorescence intensity was almost the same among the peak positions of the open areas of the left panels of FIG. 4B.

The right panels of FIG. 4B show analysis on their binding to CLEC-2 by FACS in the same way as in Example 2. The open areas depict the results of detecting $(His)_{10}$-tagged recombinant CLEC-2 bound with the wild-type Aggrus or the Aggrus mutants expressed on CHO cell surface using a fluorescent-labeled secondary antibody recognizing the His tag. The closed areas depict the results of adding a control mouse antibody instead of the $(His)_{10}$-tagged recombinant CLEC-2 protein and performing the same operation as above.

The CLEC-2 binding to the D82A-Aggrus mutant harboring the substitution of aspartic acid at position 82 by alanine (CHO/Aggrus-D82A) was found to be weaker than the binding to the D48A-Aggrus mutant harboring the substitution of aspartic acid at position 48 by alanine (CHO/Aggrus-D48A) (right panels of FIG. 4B). The D48A/D82A double mutant harboring the substitution of both aspartic acid at position 48 and aspartic acid at position 82 by alanine (CHO/Aggrus-D48A/D82A) was found to not bind to CLEC-2. These results not only suggest that the newly found PLAG4 domain on Aggrus plays an important role in the binding to CLEC-2, together with the PLAG3 domain, but suggest that PLAG4 plays a more dominant role in the binding to CLEC-2 than PLAG3.

(3) Study on Roles of PLAG3 and PLAG4 in Platelet Aggregation

Figure 4C:
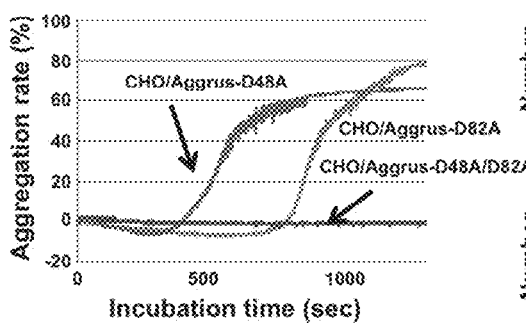
FIG. 4C is a diagram showing the effect of an amino acid mutation at position 48 (D48A), an amino acid mutant at position 82 (D82A), and a double amino acid mutation at positions 48 and 82 (D48A/D82A) on platelet aggregation.

The PLAG4 domain was found to play an important role in the binding to CLEC-2. Therefore, the role of the PLAG4 domain in platelet aggregation was then studied. As mentioned above, Aggrus binds to CLEC-2 on platelet to thereby transduce platelet aggregation-inducing signals. Whether an amino acid mutation in the PLAG4 domain would inhibit platelet aggregation was studied on the basis of Aggrus-dependent platelet aggregation-inducting activity by the platelet aggregation inhibition test described in Example 2. The results are shown in FIG. 4C.

The ability of cells expressing each mutant to aggregate platelet was studied in the same way as in Example 2 using the mutant-expressing cells CHO/Aggrus-D48A, CHO/Aggrus-D82A, and CHO/Aggrus-D48A/D82A. The platelet aggregation-inducting activity of each mutant-expressing cell was proportional to binding intensity to CLEC-2. It was found that the D82A mutant has weaker platelet aggregation-inducing activity than that of the D48A mutant, whereas the D48A/D82A double mutant exhibits no platelet aggregation-inducing activity (FIG. 4C). This demonstrated that the novel identified PLAG4 plays a dominant role in Aggrus-dependent platelet aggregation.

In order to confirm the importance of the PLAG4 domain, CHO cells were transfected with genes of mutants respectively lacking the PLAG1, PLAG3, and PLAG4 domains. Specifically, CHO cells were transfected with a plasmid prepared by integrating a pcDNA3 vector with human Aggrus cDNA encoding a mutant lacking amino acids at positions 29 to 34 in the PLAG1 region (Aggrus-Δ29-34), a plasmid prepared by integrating a pcDNA3 vector with human Aggrus cDNA encoding a mutant lacking amino acids at positions 47 to 52 in the PLAG3 region (Aggrus-Δ47-52), a plasmid prepared by integrating a pcDNA3 vector with human Aggrus cDNA encoding a mutant lacking amino acids at positions 81 to 85 in the PLAG4 region (Aggrus-Δ81-85), or a plasmid prepared by integrating a pcDNA3 vector with human Aggrus cDNA encoding a mutant lacking amino acids both at positions 47 to 52 in the PLAG3 region and at positions 81 to 85 in the PLAG4 region (Aggrus-Δ47-52/Δ81-85), to stably express the protein (see FIG. 4D). Hereinafter, the CHO cells transfected with these plasmids are referred to as CHO/Aggrus-Δ29-34, CHO/Aggrus-Δ47-52, CHO/Aggrus-Δ81-85, and CHO/Aggrus-Δ47-52/Δ81-85, respectively.

Figure 4E:
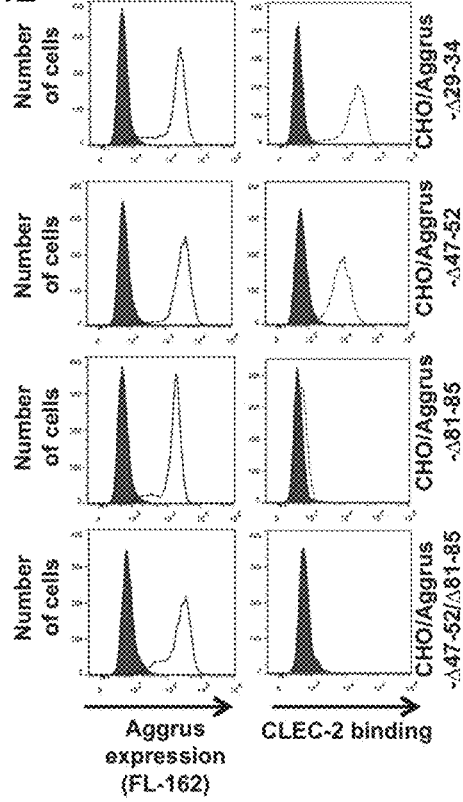
FIG. 4E is a diagram showing the expression levels and CLEC-2 protein binding capabilities of Aggrus deletion mutant proteins in transfected CHO cells.
Figure 4D:
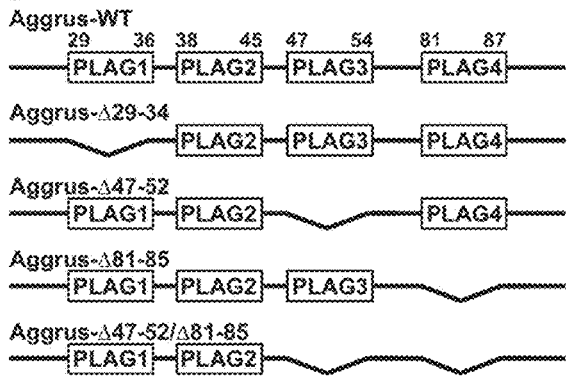
FIG. 4D is a diagram schematically showing PLAG domain-deletion mutants.

The mutant-expressing cell lines CHO/Aggrus-Δ29-34, CHO/Aggrus-Δ47-52, CHO/Aggrus-Δ81-85, and CHO/Aggrus-Δ47-52/Δ81-85 were used in FACS in the same way as in Example 2 to confirm Aggrus expression levels and reactivity with CLEC-2 (FIG. 4E). In this study, a commercially available FL-162 antibody (manufactured by Santa Cruz Biotechnology, Inc.) was used instead of the D2-40 antibody to examine the Aggrus expression levels. Also, an Alexa 488-labeled anti-rabbit IgG antibody (manufactured by Life Technologies Corp.) was used as a secondary antibody (left panels of FIG. 4E). As controls, a control rabbit antibody (manufactured by Santa Cruz Biotechnology, Inc.) is used instead of the FL-162 antibody with each cell and performing the same operation as above are shown. The open areas depict the results of staining the PLAG domain-deletion mutants of Aggrus through reaction with the FL-162 antibody, and the closed areas depict the results of reacting the control rabbit antibody instead of the FL-162 antibody. As shown in FIG. 4E (left panels), the expression levels of the Aggrus proteins on the cell surface of these transfectants were confirmed to be almost equal, also because fluorescence intensity was almost the same among the peak positions of the open areas of the panels.

The right panels of FIG. 4E show analysis on the binding to CLEC-2 by FACS in the same way as in Example 2. The open areas depict the results of detecting $(His)_{10}$-tagged recombinant CLEC-2 bound with the PLAG domain-deletion mutants of Aggrus expressed on CHO cell surface using a fluorescent-labeled secondary antibody recognizing the His tag. The closed areas depict the results of adding PBS instead of the $(His)_{10}$-tagged recombinant CLEC-2 protein and performing the same operation as above.

As in the data on the point mutants shown in FIG. 4B, it was found as to the interaction with CLEC-2 that the CLEC-2 binding to the PLAG4 domain-deletion mutant (CHO/Aggrus-Δ81-85) was weaker than the binding to the PLAG3 domain-deletion mutant (CHO/Aggrus-Δ47-52). The double mutant lacking both the PLAG3 domain and the PLAG4 domain (CHO/Aggrus-Δ47-52/Δ81-85) was found to not bind to CLEC-2.

These results not only suggest that the newly found PLAG4 domain on Aggrus plays an important role in the binding to CLEC-2, together with the PLAG3 domain, but reconfirmed that PLAG4 plays a more dominant role in the binding to CLEC-2 than PLAG3.

Example 5

Quantitative analysis on role of novel PLAG4 domain in interaction with CLEC-2 and ability to induce platelet aggregation (1) Study on Roles of PLAG3 and PLAG4 in Binding to CLEC-2

Figure 5A:
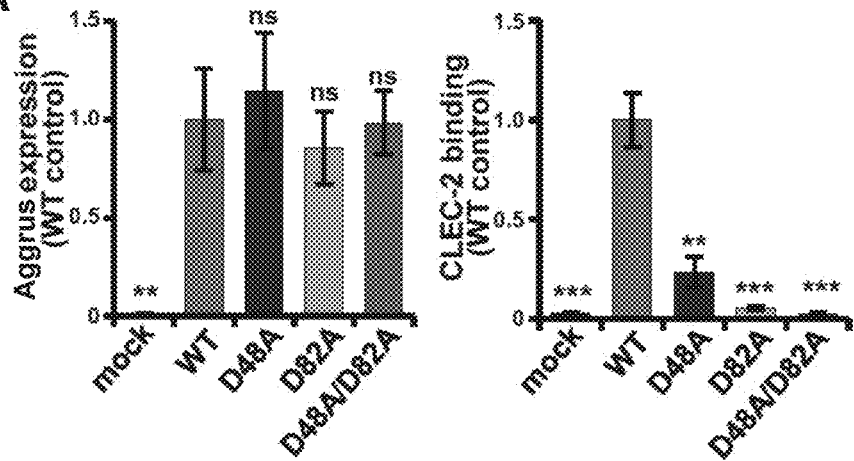
FIG. 5A is a diagram quantitatively showing the expression levels and CLEC-2 protein binding capabilities of wild-type Aggrus and Aggrus point mutant proteins in transfected CHO cells.

Aggrus expression levels and reactivity with CLEC-2 were quantitatively analyzed. Specifically, the confirmation of Aggrus expression levels and the reactivity with CLEC-2 conducted by FACS in Example 4 (see FIG. 4B) were repetitively performed three times and averaged. When average fluorescence intensity at the peak position of an open areas of CHO/Aggrus-WT was defined as 1, the expression levels of Aggrus mutant proteins are shown in a graph. As a result of statistical analysis, no significant difference was obtained (indicated by ns) in the expression levels of the Aggrus mutant proteins (D48A, D82A, and D48A/D82A) compared with the expression level of the wild-type Aggrus, showing that the expression levels were almost equal (left panels of FIG. 5A). When average fluorescence intensity at the peak position of an open area depicting reactivity with CLEC-2 was defined as 1, the reactivity of the Aggrus mutant proteins with CLEC-2 is shown in a graph. The reactivity of the Aggrus mutant proteins (D48A, D82A, and D48A/D82A) with CLEC-2 was found to be significantly decreased (, P<0.01; *, P<0.001) as compared with the reactivity of the wild-type Aggrus with CLEC-2 defined as 1 (right panels of FIG. 5A). Thus, the results of Example 4 were reproduced.

Figure 5B:
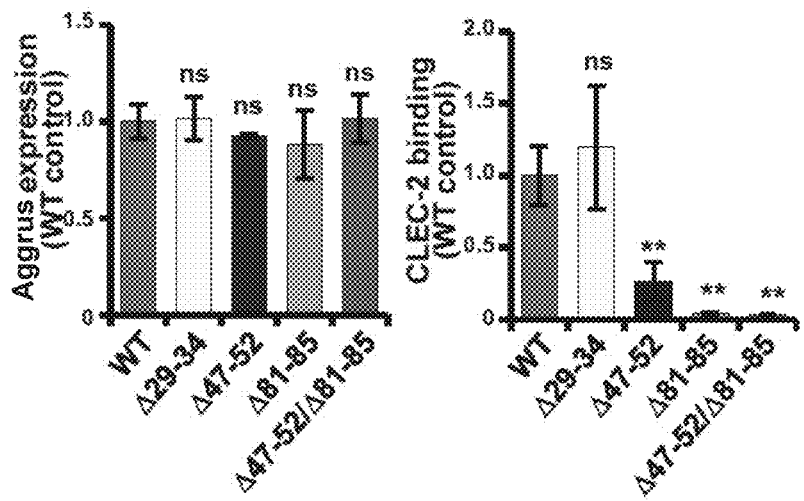
FIG. 5B is a diagram quantitatively showing the expression levels and CLEC-2 protein binding capabilities of wild-type Aggrus and Aggrus deletion mutant proteins in transfected CHO cells.

Aggrus deletion mutants were also quantitatively analyzed for their Aggrus expression levels and reactivity with CLEC-2 in the same way as above (FIG. 5B). The confirmation of Aggrus expression levels and the reactivity with CLEC-2 conducted by FACS in Example 4 (see FIG. 4E) were repetitively performed three times and averaged. When average fluorescence intensity at the peak position of an open areas of CHO/Aggrus-WT was defined as 1, the expression levels of Aggrus deletion mutant proteins are shown in a graph form. As a result of statistical analysis, no significant difference was obtained (indicated by ns) in the expression levels of the Aggrus deletion mutant proteins (Δ29-34, 447-52, Δ81-85, and Δ47-52/Δ81-85) compared with the expression level of the wild-type Aggrus, showing that the expression levels were almost equal (left panels of FIG. 5B). On the other hand, the reactivity with CLEC-2 was confirmed to be significantly decreased in the deletion mutants. When average fluorescence intensity at the peak position of an open area depicting reactivity with CLEC-2 was defined as 1, the reactivity of the Aggrus mutant proteins with CLEC-2 is shown in a graph in the right panels of FIG. 4E. The reactivity of the Aggrus deletion mutant proteins (Δ29-34, 447-52, Δ81-85, and Δ47-52/Δ81-85) with CLEC-2 was found to be significantly decreased (**, P<0.01) except for the case of Δ29-34, as compared with the reactivity of the wild-type Aggrus with CLEC-2 defined as 1 (right panels of FIG. 5B). Thus, the results of Example 4 were reproduced.

(2) Study on Roles of PLAG3 and PLAG4 in Platelet Aggregation

Figure 5C:
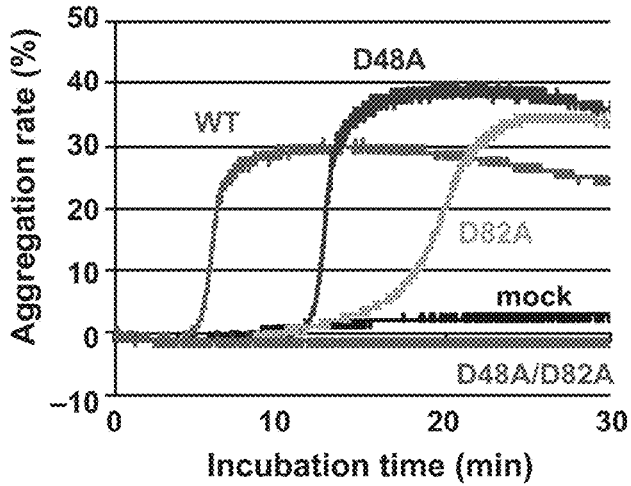
FIG. 5C is a diagram showing the effect of an amino acid mutation at position 48 (D48A), an amino acid mutant at position 82 (D82A), and a double amino acid mutation at positions 48 and 82 (D48A/D82A) on platelet aggregation.

Next, the ability of cells expressing each mutant to aggregate platelet was studied in the same way as in Example 2 using CHO/mock, CHO/Aggrus-WT, and the mutant-expressing cells CHO/Aggrus-D48A, CHO/Aggrus-D82A, and CHO/Aggrus-D48A/D82A. The reproducibility of FIG. 4C was confirmed, showing that: the platelet aggregation-inducing activity of each mutant-expressing cell is proportional to binding intensity to CLEC-2; and the D82A mutant has weaker platelet aggregation-inducing activity than that of the D48A mutant. It was further found that the D48A/D82A double mutant-expressing cells exhibit no platelet aggregation-inducing activity, as in CHO/mock (FIG. 5C). This reconfirmed that the novel identified PLAG4 plays a dominant role in Aggrus-dependent platelet aggregation.

Example 6

Involvement of E81, D82, and T85 in PLAG4 Domain in CLEC-2 Binding

The novel identified PLAG4 domain contains an EDXXT motif analogous to the PLAG3 domain. Glutamic acid (E) at position 81, aspartic acid (D) at position 82, and threonine (T) at position 85 (FIG. 6B (right panels; underlined amino acids)) in the PLAG4 domain were analyzed for their direct involvement in the binding to CLEC-2. CHO cells transfected with a plasmid prepared by integrating a pcDNA3 vector with human Aggrus cDNA encoding a mutant containing alanine replaced for glutamic acid at position 81 (CHO/Aggrus-E81A), CHO cells transfected with a plasmid prepared by integrating a pcDNA3 vector with human Aggrus cDNA encoding a mutant containing alanine replaced for aspartic acid at position (CHO/Aggrus-D82A), and CHO cells transfected with a plasmid prepared by integrating a pcDNA3 vector with human Aggrus cDNA encoding a mutant containing alanine replaced for threonine at position 85 (CHO/Aggrus-I85A) were used in analysis by FACS. CHO cells transfected with a plasmid containing wild-type human Aggrus cDNA (CHO/Aggrus-WT), and CHO cells transfected with a plasmid containing human Aggrus cDNA encoding each mutant containing alanine replaced for glutamic acid at position 47, aspartic acid at position 48, or threonine at position 52 (FIG. 6A (right panels; underlined amino acids)) in the PLAG3 domain (CHO/Aggrus-E47A, CHO/Aggrus-D48A, and CHO/Aggrus-152A) were also prepared as controls and analyzed in the same way as above.

The wild-type or mutant Aggrus-expressing CHO cells were used in FACS in the same way as in Example 2 to confirm Aggrus expression levels and reactivity with CLEC-2. As in FIG. 2, the open areas depict the results of staining the wild-type Aggrus or the Aggrus mutants through reaction with the D2-40 antibody, and the closed areas depict the results of reacting a control mouse antibody (manufactured by Sigma-Aldrich Co. LLC) instead of the D2-40 antibody. As shown in FIGS. 6A (left panels) and 6B (left panels), the expression levels of the Aggrus proteins on the cell surface of these transfectants were confirmed to be almost equal, also because fluorescence intensity was almost the same among the peak positions of the open areas of the panels.

FIGS. 6A (right panels) and 6B (right panels) show analysis on the binding of each mutant to recombinant CLEC-2 by FACS in the same way as in Example 2. The open areas depict the results of detecting (His)$_{10}$-tagged recombinant CLEC-2 bound with the wild-type Aggrus or the Aggrus mutants expressed on CHO cell surface using a fluorescent-labeled secondary antibody recognizing the His tag. The closed areas depict the results of adding the control mouse antibody instead of the (His)$_{10}$-tagged recombinant CLEC-2 protein and performing the same operation as above.

As for the interaction with CLEC-2, the CLEC-2 binding to the human Aggrus mutants harboring the substitution of glutamic acid at position 47, aspartic acid at position 48, or threonine at position 52 in the PLAG3 domain by alanine was attenuated at the same levels, when compared with the wild type. Thus, these three amino acids were confirmed to be involved in the binding to CLEC-2 (right panels of FIG. 6A). It was further found that the CLEC-2 binding of the human Aggrus mutants harboring the substitution of each of their homologous sites glutamic acid at position 81, aspartic acid at position 82, and threonine at position 85 in the PLAG4 domain by alanine was attenuated at the same levels, when compared with the wild type and the human Aggrus harboring the substitution of glutamic acid at position 47, aspartic acid at position 48, or threonine at position 52 in the PLAG3 domain by alanine (right panels of FIG. 6B).

These results show that glutamic acid at position 81, aspartic acid at position 82, and threonine at position 85 in the newly found PLAG4 domain on Aggrus are involved in the binding to CLEC-2, as with glutamic acid at position 47, aspartic acid at position 48, and threonine at position 52 in the PLAG3 domain. Also, the EDXXTS (PLAG4 domain) represented by SEQ ID NO: 4 was found to play an important role in the binding to CLEC-2.

Example 7

Preparation of Hybridoma Producing Anti-Human Aggrus Monoclonal Antibody Recognizing Novel PLAG4 Domain Hybridomas producing anti-human Aggrus monoclonal antibodies recognizing the PLAG4 domain were prepared as follows.

(1) Immunogen

A human Aggrus cDNA region encoding site from a threonine residue at position 76 to a threonine residue at position 89 (sequence: Thr Gly Ile Arg Ile Glu Asp Leu Pro Thr Ser Glu Ser Thr) was tandemly connected 12 or 40 times and cloned into a pGEX-6P-3 vector (manufactured by GE Healthcare Japan Corp.), and a GST-tagged immunogen was obtained. E. coli BL21 (DE3) was transformed with this plasmid, and a GST tag-fused recombinant protein expressed thereby was purified with glutathione Sepharose.

(2) Sensitization

A mixed solution of the obtained immunogen at 100 μg/mouse and TiterMax Gold (manufactured by TiterMax USA, Inc.) was subcutaneously administered to the necks of 6-week-old female BALB/c mice (purchased from Charles River Laboratories Japan, Inc.). For booster, the immunogen was intraperitoneally administered at 100 μg/mouse a total of 9 times on alternating weeks. Also, some sensitization was examined by a method of administering the immunogen twice to the tail roots of female BDF-1 mice (purchased from CLEA Japan Inc.).

(3) Establishment of Hybridoma

According to a routine method, spleen cells or iliac lymph node cells were collected from the immunized mice and fused with a mouse myeloma cell line P3U1 using polyethylene glycol 4000. The fused hybridomas were allowed to grow by culture in S-Clone Cloning Medium (manufactured by EIDIA Co., Ltd) containing hypoxanthine, aminopterin, and thymidine to successfully establish a plurality of hybridomas, including PG4D1 and PG4D2, producing antibodies against the PLAG4 domain. A plurality of hybridomas including 6G42A4 and 9D62D6 were successfully established from the iliac lymph node cells.

Example 8

Analysis on Properties of Anti-Human Aggrus Monoclonal Antibody Recognizing Novel PLAG4 Domain (1) Search for Epitope Human Aggrus cDNA lacking amino-terminal 24 amino acids including a signal peptide was cloned into a pGEX-6P-3 vector to prepare a GST-tagged wild-type Aggrus protein expression vector. Hereinafter, the expressed recombinant protein is referred to as ΔN24-WT. Also, codon sets corresponding to the immunogenic amino acids at positions 76 to 89 were substituted one by one by codons encoding alanine using QuikChange Site-Directed Mutagenesis Kit (manufactured by Agilent Technologies, Inc.) to prepare alanine mutant Aggrus expression vectors. Hereinafter, a recombinant mutant prepared by, for example, the mutation of an amino acid threonine (T) at position 76 to alanine (A) is referred to as ΔN24-T76A.

*E. coli*, BL21 (DE3), was transformed with each prepared plasmid and cultured. *E. coli* homogenates were used as samples to examine the reactivity of MS-1, PG4D1, PG4D2, 6G42A4, 9D62D6, and an anti-GST (alpha-GST) antibody (manufactured by Abcam plc) with the recombinant human Aggrus proteins by Western blot. As a result, as shown in FIG. 7A, the MS-1 antibody and the anti-GST antibody recognized all the Aggrus proteins including the mutants, whereas the PG4D1 antibody and the PG4D2 antibody exhibited only low reactivity with the Aggrus mutants harboring the substitution of each of 5 amino acids from arginine at position 79 to leucine at position 83 by alanine. The 6G42A4 antibody and the 9D62D6 antibody exhibited only low reactivity with the Aggrus mutants harboring the substitution of each of 7 amino acids from glycine at position 77 to leucine at position 83 by alanine except for the Aggrus mutant harboring the substitution of isoleucine at position 80 by alanine. The recognizing ability of the 9D62D6 antibody was found to be attenuated when proline at position 84 was substituted by alanine.

Accordingly, as shown in the lower row of FIG. 7A, the region recognized by the prepared antibodies was a peptide moiety from positions 77 to 84 (sequence: Gly Ile Arg Ile Glu Asp Leu Pro) indicated by the open characters, and the smallest epitope recognized by the PG4D1 antibody and the PG4D2 antibody was a peptide moiety from positions 79 to 83 (sequence: Arg Ile Glu Asp Leu), demonstrating that these peptide moieties overlap partially with the novel PLAG4 domain (sequence from positions 81 to 85 (in FIG. 7A, the sequence boxed by the dotted line: Glu Asp Leu Pro Thr) having homology to the PLAG domain shown in FIG. 3B.

(2) Study on Reactivity with Aggrus Protein Expressed in Mammalian Cells

Unlike Aggrus expressed in *E. coli*, human Aggrus expressed in mammalian cells is known to be glycosylated at many sites. The reactivity of the novel developed PG4D1 antibody and PG4D2 antibody with human Aggrus expressed in mammalian cells was studied using a surface plasmon resonance analysis apparatus Biacore X100 (manufactured by GE Healthcare Japan Corp.). A commercially available recombinant Aggrus protein (human IgG1 Fc-tagged protein; manufactured by R&D Systems, Inc.) purified from mammalian cells was immobilized by the amine coupling method onto a sensor chip CM5 coated with carboxymethyl dextran to obtain an immobilized amount corresponding to 520 RU (for assay on the PG4D1 antibody) or 600 RU (for assay on the PG4D2 antibody).

The assay was conducted by filling the flow channel with a HBS-EP+ buffer (manufactured by GE Healthcare Japan Corp.) under conditions involving 25° C. and a flow rate of 30 μL/min. Specifically, the PG4D1 antibody and the PG4D2 antibody were each diluted into 6.25 nM, 12.5 nM, 25 nM, 50 nM, and 100 nM, and flowed on the Aggrus protein-immobilized sensor chip CM5 for 60 seconds while binding reaction was observed. Subsequently, a HBS-EP+ buffer was flowed for 120 seconds while dissociation reaction was observed. The data obtained by the assay is shown in FIG. 7B.

All the developed antibodies recognized and bound to the Aggrus protein (association rate constant ($k_a$)=3×10$^4$). Furthermore, substantially no dissociation reaction was observed by the flowing of HBS-EP+ buffer for washing, and the dissociation rate constant ($k_d$) was equal to or lower than the measurement limit of the Biacore X100 used, i.e., $k_d$ 10$^{-5}$. Accordingly, the dissociation constants ($K_D$) of the PG4D1 antibody and the PG4D2 antibody were ≤3×10$^{-10}$ M, demonstrating that these antibodies exhibit very strong binding ability.

(3) Ability to Recognize Endogenously Aggrus-Expressing Cell

The MS-1 antibody can rarely recognize human bladder squamous cell carcinoma cell line UM-UC-5 cells, human fibrosarcoma cell line HT1080 cells, etc. that endogenously express Aggrus at the mRNA level. Therefore, target cancer type to be treated with the MS-1 antibody is limited. The newly developed PG4D1 antibody and PG4D2 antibody were examined for whether to be able to recognize endogenously expressed Aggrus on the surface of UM-UC-5 cells or HT1080 cells, which cannot be recognized by the MS-1 antibody. Analysis by FACS was conducted using UM-UC-5 and HT1080 cells as target cells, PG4D1 and PG4D2 antibodies as primary antibodies, and an Alexa 488-labeled anti-mouse IgG antibody as a secondary antibody. As a result, the PG4D1 antibody and the PG4D2 antibody were confirmed to be able to recognize both UM-UC-5 and HT1080 cells, which cannot be recognized by the MS-1 antibody (FIG. 7C).

Example 9

Study on Recognition Site of Anti-Human Aggrus Monoclonal Antibody Recognizing Novel PLAG4 Domain, and Reactivity Thereof In Example 8 (see FIG. 7A), the reactivity with the human Aggrus protein expressed in *E. coli* was examined. As a result, as shown in the lower row of FIG. 7A, the region recognized by the PG4D1 antibody and the PG4D2 antibody was found to be a peptide moiety from positions 77 to 84 (sequence: Gly Ile Arg Ile Glu Asp Leu Pro) indicated by the open characters. Accordingly, in order to confirm the ability to recognize glycosylated Aggrus expressed in mammalian cells, and a recognition site thereof, cell lysates of CHO cells transfected with a plasmid prepared by integrating a pcDNA3 vector with human wild-type Aggrus cDNA, Aggrus deletion mutants or Aggrus point mutants were used as samples to study the reactivity of the PG4D1 antibody and the PG4D2 antibody by Western blot.

As a result, as shown in FIG. 8A, the PG4D1 antibody and the PG4D2 antibody were confirmed to not recognize the Aggrus mutant lacking 5 amino acids at positions 81 to 85 corresponding to the PLAG4 domain. As shown in FIG. 8B, the PG4D1 antibody did not recognize the D82A-Aggrus mutant harboring the substitution of aspartic acid at position 82 in the PLAG4 domain by alanine, whereas the PG4D2 antibody was confirmed to weakly recognize the D82A-Aggrus mutant. This is consistent with the fact shown in FIG. 7A that as a result of investigating the reactivity with the human Aggrus protein expressed in *E. coli*, the PG4D2 antibody weakly recognized the D82A-Aggrus mutant. As is also evident from the results of Western blot analysis (FIGS. 8A and 8B) using an antibody recognizing α-tubulin, the protein concentrations in the electrophoresed cell lysates were the same.

In Example 8 (see FIG. 7B), whether or not to be nonspecific binding was not examined. Therefore, the reactivity of the PG4D1 antibody (subclass: mouse IgG1) and the PG4D2 antibody (subclass: mouse IgG2a) with human Aggrus was examined using a surface plasmon resonance analysis apparatus Biacore X100 (manufactured by GE Healthcare Japan Corp.) as well as control mouse IgG1 (manufactured by Sigma-Aldrich Co. LLC) and control mouse IgG2a (manufactured by Sigma-Aldrich Co. LLC) to be compared therewith (FIGS. 8C and 8D). Specifically, a commercially available purified recombinant Aggrus protein (human IgG1 Fc-tagged protein; manufactured by R&D Systems, Inc.) was immobilized by the amine coupling method onto a sensor chip CM5 coated with carboxymethyl dextran to obtain an immobilized amount corresponding to 562.2 RU (for assay on the PG4D1 antibody). The assay was conducted by filling the flow channel with a HBS-EP+ buffer (manufactured by GE Healthcare Japan Corp.) under conditions involving 25° C. and a flow rate of 30 µL/min. Specifically, the control mouse IgG1 (Control IgG1) was diluted into 3.7 nM, 11.1 nM, 33.3 nM, 100 nM, and 300 nM, and flowed on the Aggrus protein-immobilized sensor chip CM5 for 60 seconds while binding reaction was observed. Subsequently, a HBS-EP+ buffer was flowed for 1800 seconds while dissociation reaction was observed. Subsequently, the PG4D1 antibody was flowed under the same conditions using the same sensor chip CM5 as above while binding reaction was observed. The data obtained by the assay is shown in FIG. 8C.

Next, control mouse IgG2a (Control IgG2a) and subsequently the PG4D2 antibody were flowed under the same conditions as above on a sensor chip CM5 having an immobilized amount corresponding to 562.6 RU (for assay on the PG4D2 antibody) while binding reaction was observed. The data obtained by the assay is shown in FIG. 8D.

Both the control mouse IgG1 and the control mouse IgG2a were confirmed to not bind to the Aggrus-immobilized sensor chip, whereas both the PG4D1 antibody and the PG4D2 antibody were confirmed to exhibit strong binding, as in Example 8 (see FIG. 7B), demonstrating that the binding of the PG4D1 antibody and the PG4D2 antibody to the Aggrus-immobilized sensor chip is not nonspecific binding. In this assay, the dissociation constants ($K_D$) of the PG4D1 antibody and the PG4D2 antibody were ≤3×10$^{-10}$ M, as in Example 8 (see FIG. 7B), demonstrating that these antibodies exhibit very strong binding.

Example 10

Inhibition of Binding Between Aggrus and CLEC-2 by PG4D1 and PG4D2 Antibodies (1) Study by AlphaScreen Method The monoclonal antibodies PG4D1 and PG4D2 obtained by the present invention were analyzed for their inhibitory effects on the binding between Aggrus and CLEC-2 by use of the nonradioactive homogeneous proximity assay AlphaScreen® method.

1 ng of a purified recombinant Aggrus protein (human IgG1 Fc-tagged protein, manufactured by R&D Systems, Inc.) and 30 ng of a purified recombinant CLEC-2 protein ((His)$_{10}$-tagged protein; rCLEC-2, manufactured by R&D Systems, Inc.) were dispensed to 96-well plates, and control mouse IgG1 (manufactured by Sigma-Aldrich Co. LLC), control mouse IgG2a (manufactured by Sigma-Aldrich Co. LLC), and the MS-1, PG4D1, PG4D2, 6G42A4, and 9D62D6 antibodies were added thereto such that their final concentrations were 12.5 µg/mL to 5 ng/mL. After the addition, the antibodies were reacted at 26° C. for 1 hour. Then, Nickel Chelate AlphaScreen Donor Beads and Protein A AlphaLISA Acceptor Beads diluted with AlphaLISA Universal Buffer were added thereto and further reacted at 26° C. for 1 hour, followed by excitation with laser having a wavelength of 680 nm using Envision (manufactured by PerkinElmer, Inc.).

By the excitation, Donor Beads convert oxygen to a singlet state, and this oxygen in a singlet state activates fluorescent materials contained in acceptor beads located in proximity thereto to thereby emit a fluorescence signal of 615 nm. Specifically, the fluorescence signal is emitted, provided that the His-tagged CLEC-2 protein bound with Nickel Chelate AlphaScreen Donor Beads and the Fc-tagged recombinant Aggrus protein bound with Protein A AlphaLISA Acceptor Beads are located in proximity to each other. Thus, this fluorescence signal can be quantified to thereby quantify the binding state between Aggrus and CLEC-2.

When the fluorescence signal intensity without antibody addition was defined as 100%, all the added PG4D1 antibody, PG4D2 antibody, and MS-1 antibody were confirmed, as shown in FIG. 9A, to inhibit the binding of Aggrus to CLEC-2 in a concentration-dependent manner. Particularly, the PG4D1 antibody and the PG4D2 antibody were found to have stronger inhibitory activity than that of the MS-1 antibody. Although the inhibition activity of the binding between Aggrus and CLEC-2 was also observed in the 6G42A4 and 9D62D6 antibodies, the effect was weaker than that of the MS-1 antibody (FIG. 9B).

This result shows that the peptide moiety from positions 77 to 84, which is a region recognized as an epitope by the antibodies, is important for the binding of Aggrus to CLEC-2. Also, it is evident from the analysis of Example 6 using the point mutants that threonine at position 85 is important for the binding of Aggrus to CLEC-2. Thus, it was concluded that the amino acid sequence from positions 77 to 85 (SEQ ID NO: 1: GIRIEDLPT) is a sequence important for the binding of Aggrus to CLEC-2.

The region represented by SEQ ID NO: 1 is a region necessary for the binding of Aggrus to CLEC-2, and the region of SEQ ID NO: 3 (RIEDL) recognized by the PG4D1 antibody and the PG4D2 antibody is considered to be a core region thereof. Thus, a peptide comprising the region of SEQ ID NO: 1 or SEQ ID NO: 3 can be synthesized and administered to thereby inhibit the binding between CLEC-2 and Aggrus and inhibit the binding between CLEC-2 and Aggrus. If the binding between CLEC-2 and Aggrus can be inhibited, platelet aggregation can be inhibited and cancer progression and metastasis can be inhibited. Therefore, a pharmaceutical composition containing the region as an active ingredient is obtained.

The peptide necessary for competitive inhibition can be any peptide comprising the region of SEQ ID NO: 1 or 3. It is preferred that the peptide should not be much large, in consideration of the synthesis or effect of the peptide. Specifically, a peptide that comprises the region of SEQ ID NO: 1 or 3 and has a peptide sequence longer by approximately several amino acids to several tens of amino acids than the region is preferred, and the peptide sequence of SEQ ID NO: 1 or 3 itself is more preferred.

(2) Study by FACS

The inhibition of the binding between Aggrus and CLEC-2 by the PG4D1 antibody and the PG4D2 antibody was analyzed by FACS. The analysis was conducted on whether the anti-Aggrus monoclonal antibodies would inhibit the binding of CHO/Aggrus-WT cells to recombinant CLEC-2 (rCLEC-2). Detection was performed using an antibody recognizing a His tag on the recombinant CLEC-2.

Specifically, the CHO/Aggrus-WT cells were recovered from a culture vessel, washed with PBS, and then adjusted to a cell density of 1.5×10$^5$ cells/ml. To 100 µL of the reaction solution, mouse control IgG (100 µg/mL; a sample of w/o rCLEC-2 or rCLEC-2 alone), the PG4D1 antibody (100 μg/mL; PG4D1+rCLEC-2 sample), the PG4D2 antibody (100 μg/mL: PG4D2+rCLEC-2 sample), or the MS-1 antibody (100 μg/mL; MS-1+rCLEC-2 sample) was added, and reacted on ice for 30 minutes. Then, the cells were washed with PBS, and 0.4 μg/mL $(His)_{10}$-tagged recombinant CLEC-2 protein (rCLEC-2) purified from mammalian cells was then added to the samples except for w/o rCLEC-2, and reacted on ice for 30 minutes. After washing with PBS, a fluorescent-labeled secondary antibody recognizing the His tag was added thereto and further reacted on ice for 30 minutes. Finally, the cells were washed with PBS three times, followed by analysis using Cytomics FC500. As a result, as shown in FIG. 10A, the PG4D1 antibody and the PG4D2 antibody inhibited the binding of rCLEC-2 to the Aggrus-expressing cells, as with the MS-1 antibody, while the large shift of the peaks to the left was confirmed because their inhibitory activity was stronger than that of the MS-1 antibody.

The MS-1 antibody recognizes a region over the PLAG2 and PLAG3 domains (see FIG. 1), whereas the PG4D1 antibody and the PG4D2 antibody recognize a region over the PLAG4 domain and its neighborhood (see FIG. 7). Accordingly, change in the ability of the MS-1 antibody to recognize Aggrus upon binding of the PG4D1 antibody or the PG4D2 antibody to Aggrus was examined. A DyLight594-labeled MS-1 antibody and a DyLight594-labeled PG4D2 antibody were prepared. Specifically, the MS-1 antibody and the PG4D2 antibody were fluorescently labeled using DyLight 594 Microscale Antibody Labeling Kit (manufactured by Life Technologies Corp.) according to the instruction.

The CHO/Aggrus-WT cell line was recovered from a culture vessel, washed with PBS, and then adjusted to a cell density of $1.5 \times 10^5$ cells/ml. The DyLight594-labeled MS-1 antibody or the DyLight594-labeled PG4D2 antibody was added thereto and reacted on ice for 30 minutes. For some samples, a non-labeled MS-1 antibody or PG4D2 antibody was added in adding the DyLight594-labeled antibody. Then, the cells were washed with PBS three times, followed by analysis using Cytomics FC500. The closed areas depict results of reacting a non-labeled control mouse antibody (manufactured by Sigma-Aldrich Co. LLC) instead of the fluorescent-labeled antibody with the cells and performing the same operation as above.

As shown in FIG. 10B (top panels), the peaks of the open areas shifted to the right with respect to the closed areas, because the MS-1 antibody and the PG4D2 antibody were sufficiently labeled with DyLight594. The reactivity of the DyLight594-labeled MS-1 antibody with the CHO/Aggrus-WT cells was inhibited in the presence of the non-labeled MS-1 antibody in a manner dependent on the concentration of the non-labeled MS-1 antibody (left middle panel of FIG. 10B), but was not inhibited in the presence of the non-labeled PG4D2 antibody (left bottom panel of FIG. 10B). The reactivity of the DyLight594-labeled PG4D2 antibody with the CHO/Aggrus-WT cells was inhibited in the presence of the non-labeled PG4D2 antibody in a manner dependent on the concentration of the non-labeled PG4D2 antibody (right bottom panel of FIG. 10B), but was not inhibited in the presence of the non-labeled MS-1 antibody (right middle panel of FIG. 10B). This suggested that the MS-1 antibody and the PG4D2 antibody recognize the PLAG3 and PLAG4 domains, respectively, and thereby inhibit the binding between Aggrus and CLEC-2, and in other words, the PLAG3 and PLAG4 domains are independently involved in the binding to CLEC-2.

If the MS-1 antibody and the PG4D2 antibody recognize the PLAG3 and PLAG4 domains, respectively, and inhibit the binding to CLEC-2, the possibility was considered that combined use of the MS-1 antibody and the PG4D2 antibody could completely inhibit the binding between Aggrus and CLEC-2. Accordingly, in order to examine the possibility, the binding between Aggrus and CLEC-2 was analyzed by FACS using the MS-1 antibody alone and the MS-1 antibody in combination with the PG4D2 antibody. The analysis was conducted on whether the MS-1 antibody and the PG4D2 antibody would inhibit the binding of CHO/Aggrus-WT cells to recombinant CLEC-2 (rCLEC-2). Detection was performed using an antibody recognizing a His tag on the recombinant CLEC-2 (FIG. 10C).

Specifically, the CHO/Aggrus-WT cells were recovered from a culture vessel, washed with PBS, and then adjusted to a cell density of $1.5 \times 10^5$ cells/ml. To 100 μL of the reaction solution, mouse control IgG (100 μg/mL; a sample of w/o rCLEC-2 or rCLEC-2 alone), the PG4D2 antibody (100 μg/mL: PG4D2+rCLEC-2 sample), or the combination of the PG4D2 antibody and the MS-1 antibody (100 μg/mL each: PG4D2+MS-1+rCLEC-2 sample) was added, and reacted on ice for 30 minutes. Then, the cells were washed with PBS, and 0.4 μg/mL $(His)_{10}$-tagged recombinant CLEC-2 protein (rCLEC-2) purified from mammalian cells was then added to the samples except for w/o rCLEC-2, and reacted on ice for 30 minutes. After washing with PBS, a fluorescent-labeled secondary antibody recognizing the His tag was added thereto and further reacted on ice for 30 minutes. Finally, the cells were washed with PBS three times, followed by analysis using Cytomics FC500. As a result, as shown in FIG. 10C, the combined use of the PG4D2 antibody and the MS-1 antibody inhibited the binding of rCLEC-2 more strongly than the PG4D2 antibody alone, as the peak is greatly shifted to the left.

These results demonstrated that: the PLAG4 domain recognized by the PG4D1 antibody or the PG4D2 antibody is involved in the binding to CLEC-2 independently from the PLAG3 domain; and the stronger inhibition of the CLEC-2 binding is observed by combined use of an antibody recognizing the PLAG4 domain and an antibody recognizing the PLAG3 domain.

Example 11

Analysis on Inhibition of CLEC-2 Binding and Inhibition of Platelet Aggregation by PG4D1 and PG4D2 Antibodies Using Aggrus Mutant (1) Inhibition of Binding to CLEC-2

Aggrus binds to CLEC-2 on platelet to thereby transduce platelet aggregation-inducing signals. The PLAG4 domain recognized by the PG4D1 antibody or the PG4D2 antibody was examined for its direct involvement in the binding to CLEC-2 and platelet aggregation. The study was conducted using CHO cells transfected with a plasmid prepared by integrating a pcDNA3 vector with human Aggrus cDNA encoding a mutant containing alanine replaced for aspartic acid at position 48 in the PLAG3 domain (CHO/Aggrus-D48A). Use of the expressed Aggrus-D48A mutant eliminates the involvement of the PLAG3 domain of Aggrus in the binding to CLEC-2 and permits evaluation of the binding of the PLAG4 domain to CLEC-2. The direct involvement of the PLAG4 domain in the binding of Aggrus to CLEC-2 was analyzed by FACS.

The CHO/Aggrus-D48A cells were recovered from a culture vessel, washed with PBS, and then adjusted to a cell density of $1.5 \times 10^5$ cells/ml. To 100 μL of the reaction solution, PBS (sample of w/o rCLEC-2 or Add no antibody), varying concentrations of the PG4D1 antibody (left panel of FIG. 11A), or varying concentrations of the PG4D2 antibody (right panel of FIG. 11A) was added, and reacted on ice for 30 minutes. Then, the cells were washed with PBS, and 0.4 μg/mL $(His)_{10}$-tagged recombinant CLEC-2 protein (rCLEC-2) purified from mammalian cells was added to the samples except for w/o rCLEC-2, and reacted on ice for 30 minutes. After washing with PBS, a fluorescent-labeled secondary antibody recognizing the His tag was added thereto and further reacted on ice for 30 minutes. Finally, the cells were washed with PBS three times, followed by analysis using Cytomics FC500. As shown in FIG. 11A, the binding of rCLEC-2 to the Aggrus-expressing cells was found to be inhibited by the addition of the PG4D1 antibody or the PG4D2 antibody in a concentration-dependent manner, and almost completely inhibited by the addition at a concentration of 100 μg/mL. These results demonstrated that the PLAG4 domain recognized by the PG4D1 antibody or the PG4D2 antibody is directly involved in the binding to CLEC-2.

(2) Inhibition of Platelet Aggregation

Next, the binding of the PLAG4 domain to CLEC-2 was confirmed by a platelet aggregation inhibition test. Specifically, in vitro platelet aggregation analysis using washed mouse platelet was conducted by the monitoring of light transmittance using MCM HEMA TRACER 313M. As shown in FIG. 11B, the CHO/Aggrus-D48A cells induced platelet aggregation, whereas the addition of 50 ng/mL of PG4D2 antibody was observed to prevent platelet aggregation (FIG. 11B). Almost the same platelet aggregation inhibitory effect was confirmed even when the PG4D1 antibody was added beforehand (not shown). These results demonstrated that: the PLAG4 domain recognized by the PG4D1 antibody or the PG4D2 antibody is directly involved in platelet aggregation; and the newly developed antibodies are neutralizing antibodies inhibiting platelet aggregation by masking the PLAG4 domain through binding to the domain.

The difference between the PG4D1 antibody or the PG4D2 antibody recognizing the PLAG4 domain and the MS-1 antibody recognizing the PLAG3 domain, and an effect brought about by combined use of the PG4D2 antibody and the MS-1 antibody were examined by the platelet aggregation inhibition test. The in vitro platelet aggregation analysis was conducted in the same way as above using CHO/Aggrus-WT cells. As shown in FIG. 12A, the CHO/Aggrus-WT cells induced platelet aggregation, whereas platelet aggregation-starting time was observed to be delayed by the addition of 10 μg/mL MS-1 antibody, PG4D1 antibody, or PG4D2 antibody compared with the addition of a control antibody (Control IgG) (FIG. 12A). The platelet aggregation inhibitory activity of the PG4D1 antibody and the PG4D2 antibody was found to be stronger than that of the MS-1 antibody and therefore delay the aggregation-starting time.

The CHO/Aggrus-WT cell-dependent platelet aggregation was further confirmed to be almost completely inhibited by the combined use of 10 μg/mL of MS-1 antibody and 10 μg/mL of PG4D2 antibody compared with the addition of the PG4D2 antibody alone (FIG. 12B). These results demonstrated that both the PLAG4 domain recognized by the PG4D1 antibody or the PG4D2 antibody and the PLAG3 domain recognized by the MS-1 antibody are involved in platelet aggregation.

Example 12

Inhibition of Hematogenous Metastasis to Lung by PG4D1 and PG4D2 Antibodies

It is known that metastatic nodules of the lung are formed approximately 20 days after intravenous injection of CHO cells expressing human Aggrus into nude mice. The present inventors have already disclosed that Aggrus-dependent lung metastasis is inhibited by the MS-1 antibody (Patent Literature 2). Accordingly, whether Aggrus-dependent hematogenous metastasis would be inhibited by the administration of the anti-Aggrus antibody of the present invention 1 day before cell transplantation was analyzed.

The analysis was conducted using 6-week-old female BALB/c-nu nude mice (purchased from Charles River Laboratories Japan, Inc.). One day before transplantation of the CHO/Aggrus-WT cells (tumor cells), a control mouse antibody (manufactured by Sigma-Aldrich Co. LLC), MS-1 antibody, PG4D1 antibody, or PG4D2 antibody was administered at a dose of 10 μg/mouse from the mouse tail veins. On the next day, the CHO/Aggrus-WT cells were recovered from a culture vessel, washed with PBS, then adjusted to a cell density of $2.5 \times 10^6$ cells/ml, and intravenously transplanted at 100 μL/mouse. As shown in FIG. 13, the formation of lung metastasis of the CHO/Aggrus-WT cells was remarkably inhibited by the administration of PG4D1 antibody or PG4D2 antibody on the day before tumor inoculation, as with the administration of MS-1 antibody on the day before tumor inoculation. Thus, PG4D1 antibody and PG4D2 antibody were found to not only have Aggrus-neutralizing activity but strongly inhibit Aggrus-dependent hematogenous metastasis.

Similar study was conducted using an isotype matched control antibody having a subclass identical to that of each antibody. This study was conducted using 8 mice of 5-week-old female BALB/c-nu nude mice per group (purchased from Charles River Laboratories Japan, Inc.). One day before transplantation of the CHO/Aggrus-WT cells (tumor cells), control mouse IgG1 (Control IgG1, manufactured by Sigma-Aldrich Co. LLC), control mouse IgG2a (Control IgG2a, manufactured by Sigma-Aldrich Co. LLC), PG4D1 antibody, PG4D2 antibody, or MS-1 antibody was administered at a dose of 10 μg/mouse from the mouse tail veins. On the next day, the CHO/Aggrus-WT cells were recovered from a culture vessel, washed with PBS, then adjusted to a cell density of $2.5 \times 10^6$ cells/ml, and intravenously transplanted at 100 μL/mouse. 19 days later, their lungs were harvested and analyzed. As shown in FIG. 14A, photographs were taken after staining using picric acid to visualize the metastatic foci. In addition, the number of metastatic foci on the lung surface was counted (FIG. 14B). The lung metastasis of the CHO/Aggrus-WT cells was confirmed to be significantly inhibited (**, $P<0.01$) by the administration of PG4D1 antibody or PG4D2 antibody on the day before tumor inoculation, as with MS-1 antibody, as compared with each isotype matched control antibody administration group.

Thus, the PG4D1 antibody and the PG4D2 antibody were found to not only have activity of neutralizing Aggrus-dependent platelet aggregation but strongly inhibit Aggrus-dependent hematogenous metastasis. It has been reported that platelet aggregation is involved in the metastatic niche formation (formation of metastatic microenvironments) of cancer cells. From this, PG4D1 antibody and PG4D2 antibody are considered to be effective for inhibiting niche formation associated with metastasis. Furthermore, the involvement of platelet in tumor growth in primary foci has also been shown. Therefore, it is also suggested that PG4D1 antibody and PG4D2 antibody exert a metastasis inhibitory effect by inhibiting the growth of metastatic cancer in a metastatic organ.

Example 13

Demonstration of Effect of Inhibiting Lung Metastasis of LC-SCC-015 Cell by PG4D2 Antibody Recognizing PLAG4 Domain The human lung squamous cell carcinoma cell line LC-SCC-015 established by the present inventors were transplanted to 5-week-old male CB-17 SCID mice (purchased from Charles River Laboratories Japan, Inc.) (3 mice per group). Specifically, one day before transplantation of the LC-SCC-015 cells (tumor cells), control mouse IgG2a (Mouse IgG2a, manufactured by Sigma-Aldrich Co. LLC) or PG4D2 antibody was intravenously administered at a dose of 30 µg/mouse. On the next day, the LC-SCC-015 cells were recovered from a culture vessel, washed with PBS, then adjusted to a cell density of $2.5\times10^6$ cells/ml, and transplanted at 100 µL/mouse from the tail veins. 31 days later, their lungs were harvested and stained using picric acid to visualize the metastatic foci, and the number of metastatic foci on the lung surface was then counted (FIG. 15). Lung metastasis was confirmed to be significantly inhibited (*, $P<0.05$) by the administration of PG4D2 antibody on the day before tumor inoculation, even when compared with the control mouse IgG2a antibody administration group.

Not only did the PG4D2 antibody have activity of neutralizing Aggrus-dependent platelet aggregation, but the involvement of Aggrus-dependent platelet aggregation in hematogenous lung metastasis was also confirmed for the lung metastasis of the established human lung squamous cell carcinoma cell line LC-SCC-015. The PG4D2 antibody was found to inhibit the lung metastasis of the LC-SCC-015 cells by strongly inhibiting Aggrus-dependent hematogenous metastasis.

It has been reported that platelet aggregation is involved in the metastatic niche formation (formation of metastatic microenvironments) of cancer cells. From this, the PG4D2 antibody is considered to be also effective for inhibiting niche formation associated with metastasis. Furthermore, the involvement of platelet in tumor growth in primary foci has also been shown. Therefore, it is also suggested that the PG4D2 antibody exerts a metastasis inhibitory effect by inhibiting the growth of metastatic cancer in a metastatic organ.

Example 14

Examination of Effect of Inhibiting PC-10 Tumor Growth by PG4D2 Antibody Recognizing PLAG4 Domain A human lung squamous cell carcinoma cell line PC-10 was subcutaneously transplanted into 5-week-old male NOD SCID mice (NOD.CB17-Prkdcscid/J; purchased from Charles River Laboratories Japan, Inc.) (4 or 5 mice per group). When tumor volumes reached approximately 80 mm$^3$ 11 days after the PC-10 cell transplantation, the mice were grouped such that the tumor volumes were almost equalized among the groups. Then, control mouse IgG2a (Control IgG2a, manufactured by Sigma-Aldrich Co. LLC) at a dose of 200 µg/mouse (n=5), PG4D2 antibody at a dose of 100 µg/mouse (n=4), MS-1 antibody at a dose of 100 µg/mouse (n=5), or the combination of PG4D2 antibody and MS-1 antibody at a total dose of 200 µg (100 µg each)/mouse (n=4) was intravenously administered. When the start day of antibody administration was defined as 0 days, the same amount as above of the antibody was administered 3, 7, 10, 14, 17, 21, and 24 days later.

As shown in FIG. 16, tumor growth was inhibited in the PG4D2 antibody or MS-1 antibody administration group compared with the control mouse antibody administration group. The same tendency was obtained in the case of combo treatment with PG4D2 antibody and MS-1 antibody. Slight enhancement in tumor inhibitory effect was observed in the combined use. Although the complete regression of tumor was observed in one mouse each of the PG4D2 antibody administration groups (the group given PG4D2 antibody alone and the group given PG4D2 antibody and MS-1 antibody in combination), these mice were excluded from the calculation of average tumor volumes in consideration of the possibility of the specificity of PC-10 cells or difference among mouse individuals. However, because the tumor regression was observed only in the PG4D2 antibody administration groups, there is a possibility that PG4D2 antibody has a strong antitumor effect different from that of MS-1 antibody.

In this study, NOD SCID mice, which are severe combined immunodeficient mice, were used. The nude mice used in Example 12 or the SCID mice used in Example 13 are mice deficient in T cells and B cells, whereas the NOD SCID mice are not only deficient in T cells and B cells but have reduced NK activity. Thus, the antitumor effects of the Aggrus-neutralizing antibodies observed in the experiment of Example 14 using the NOD SCID mice are considered to depend on neither the ADCC activity nor CDC activity of the antibodies. It was suggested that the antibodies recognizing the PLAG3 or PLAG4 domain, used here, neutralize the platelet aggregation-inducting activity of Aggrus and thereby inhibit the release of various growth factors from platelet, consequently causing the inhibition of growth. Accordingly, it was suggested that PG4D2 antibody inhibits tumor growth in primary foci by indirectly exhausting growth factors, not by directly killing PC-10 cells. Therefore, the antibody recognizing the PLAG4 domain was found to not only inhibit hematogenous metastasis as shown in Examples 12 and 13 but inhibit tumor growth in primary foci.

Example 15

Study on Aggrus-Neutralizing Activity of Human-Mouse Chimeric PG4D2 Antibody

A gene encoding the antigen recognition site of the PG4D2 antibody was cloned and linked to a gene encoding the Fc site of human IgG4 to prepare an IgG4-type human-mouse chimeric PG4D2 antibody (Ch.PG4D2-IgG4SP). Also, the cloned gene was linked to a gene encoding the Fc site of human IgG1 to prepare an IgG1-type human-mouse chimeric PG4D2 antibody (Ch.PG4D2-IgG1).

FIG. 17A shows results of examining the reactivity of each antibody recognizing Aggrus in the same way as in Example 2 using CHO/Aggrus-WT cells. The left panel shows results of reacting the CHO/Aggrus-WT cells with the non-chimeric mouse antibody PG4D2 antibody at the concentrations shown in the drawing, and washing the cells with PBS, followed by reaction with Alexa 488-labeled anti-mouse IgG (anti-mouse IgG-Alexa488) as a secondary antibody. The middle panel shows results of reacting the CHO/Aggrus-WT cells with the IgG4-type human-mouse chimeric PG4D2 antibody (Ch.PG4D2-IgG4SP) at the concentrations shown in the drawing, and washing the cells with PBS, followed by reaction with Alexa 488-labeled anti-human IgG (anti-human IgG-Alexa488) as a secondary antibody. The right panel shows results of reacting the CHO/Aggrus-WT cells with the IgG1-type human-mouse chimeric PG4D2 antibody (Ch.PG4D2-IgG1) at the concentrations shown in the drawing, and washing the cells with PBS, followed by reaction with Alexa 488-labeled anti-human IgG as a secondary antibody. The chimeric antibodies Ch.PG4D2-IgG4SP and Ch.PG4D2-IgG1 were confirmed to exhibit reactivity with Aggrus.

FIG. 17B shows results of analyzing the inhibition of the binding of Aggrus to CLEC-2 by FACS in the same way as in Example 10. The assay was conducted using the non-chimeric mouse antibody PG4D2 antibody (upper panel of FIG. 17B), the IgG4-type human-mouse chimeric PG4D2 antibody (Ch.PG4D2-IgG4SP) (lower left panel of FIG. 17B), and the IgG1-type human-mouse chimeric PG4D2 antibody (Ch.PG4D2-IgG1) (lower right panel of FIG. 17B). In each assay, an antibody of the same species and subclass was used as a control antibody. Specifically, Control mouse IgG2a (manufactured by Sigma-Aldrich Co. LLC), Control human IgG4 (manufactured by Sigma-Aldrich Co. LLC), and Control human IgG1 (manufactured by Sigma-Aldrich Co. LLC) were used.

As a result, the IgG4-type human-mouse chimeric PG4D2 antibody (Ch.PG4D2-IgG4SP) exhibited Aggrus-neutralizing activity almost equivalent to the original non-chimeric mouse antibody, PG4D2 antibody, whereas the IgG1-type human-mouse chimeric PG4D2 antibody (Ch.PG4D2-IgG1) had weaker Aggrus-neutralizing activity. Therefore, although the necessary amount of the antibody Ch.PG4D2-IgG1 for inhibiting the binding to CLEC-2 was larger than that of the original PG4D2 antibody, 60 µg/mL of Ch.PG4D2-IgG1 was sufficient for reaction to inhibit the binding of Aggrus to rCLEC-2.

Example 16

Immunostaining Using Osteosarcoma Tissue Section and Using PG4D1 Antibody and PG4D2 Antibody Bone and cartilage malignant tumor tissue microarray, containing 4 cases of malignant tumor (2 each of chondrosarcoma, osteosarcoma and Ewing's sarcoma), quadruple cores per case (product No. T264a) was purchased from US Biomax, Inc., and HE staining was performed according to a routine method (FIG. 18A).

In this tissue array, four sections per case of two each of chondrosarcoma, osteosarcoma, and Ewing's sarcoma tissue samples, and pheochromocytoma as a tissue marker are located, and protein expression in tumor tissues of patients differing in disease stage can be analyzed by immunostaining. Two osteosarcoma cases mounted on this slide were used to study the ability of D2-40, PG4D1, and PG4D2 to recognize osteosarcoma by immunostaining.

The immunostaining was performed by the following method using a D2-40 monoclonal antibody (Dako; product No. M3619, Anti-podoplanin mouse monoclonal antibody), PG4D1 antibody (5 mg/ml), or PG4D2 antibody (5 mg/ml) as a primary antibody. Specifically, the slide was deparaffinized, then washed with water, dipped in 0.3% hydrogen peroxide water/methanol at room temperature for 10 minutes, and washed with PBS for 5 minutes three repetitive times. Then, the slide was dipped in Blocking One P (manufactured by Nacalai Tesque, Inc., #05999-84) at room temperature for 15 minutes and then washed with PBS for 5 minutes. In the case of using D2-40 antibody as a primary antibody, this antibody was then diluted 1/100 with PBS and incubated at 4° C. for 16 hours. In the case of using PG4D1 or PG4D2 antibody as a primary antibody, this antibody was diluted 1/1000 with PBS (final antibody concentration: 5 µg/ml) and incubated at 4° C. for 16 hours. For D2-40 antibody, it was difficult to calculate its amount on a gram scale because a culture supernatant was used. Therefore, as given below, antibody concentrations were selected for staining such that the degree of staining of a control tissue was equivalent among all the antibodies. After washing with PBS for 5 minutes three repetitive times, One-Step Polymer-HRP (manufactured by BioGenex Laboratories, Inc., # HK595-50K) was reacted therewith as a secondary antibody at room temperature for 15 minutes. After washing with PBS for 5 minutes three repetitive times, color was developed for 5 minutes using DAB (trade name: Super Sensitive DAB (Ready to use), manufactured by BioGenex Laboratories, Inc., # HK542-XAK). After washing with water, the nuclei were counterstained by dipping in a Mayer's hematoxylin solution (manufactured by Muto Pure Chemicals Co., Ltd., #3000-2) for 1 minute, followed by washing with water, dehydration, clearing, and mounting according to routine methods.

As mentioned above, the tumor tissues of two osteosarcoma cases are mounted on the T264a slide serving as a tissue array. The tumor tissues of A3 and A6 shown in FIG. 18A are derived from the first osteosarcoma case (10-year-old male), and the tumor tissues of B1 and B4 are derived from the second osteosarcoma case (21-year-old female). As shown in FIG. 18B, under comparison conditions where the degree of staining of the control tumor tissue (pheochromocytoma) positioned at D7 was almost equal among the antibodies, the degree of immunostaining using PG4D1 antibody or PG4D2 antibody was larger than the degree of staining with D2-40 antibody, demonstrating that PG4D1 antibody and PG4D2 antibody have the higher ability to recognize osteosarcoma than that of D2-40 antibody. This suggests that these antibodies are useful as drugs inhibiting the growth or metastasis of at least osteosarcoma.

Aggrus expression can be confirmed at the mRNA level, but may not be detected using an antibody. Thus, there have been concerns about the limited therapeutic application of antibodies against Aggrus. For example, the present inventors showed that PG4D1 antibody and PG4D2 antibody recognize the human bladder squamous cell carcinoma cell line UM-UC-5 cells or the human fibrosarcoma cell line HT1080 cells, which cannot be recognized by MS-1 antibody (FIG. 7C). Although the mechanism under which Aggrus may or may not be recognized depending on the type of cancer is unknown, it is considered that PG4D1 antibody and PG4D2 antibody can be applied to the treatment of at least osteosarcoma shown here as well as bladder squamous cell carcinoma, fibrosarcoma, and lung squamous cell carcinoma for which the binding was proved in the experimental systems using cell lines.

As described above, an anti-Aggrus antibody binding to the region represented by SEQ ID NO: 1 inhibits the binding of Aggrus to CLEC-2 and thereby inhibits platelet aggregation and inhibits cancer progression or metastasis. Furthermore, a drug inhibiting the binding to CLEC-2 can be screened for by using the binding of this region to CLEC-2 as an index.

Deposition No.

NITE P-02070

NITE P-02071

The invention claimed is:

1. A neutralizing monoclonal antibody or a fragment consisting of a functional fragment thereof, wherein the monoclonal antibody is produced by a hybridoma of deposition No. NITE BP-03041 (PG4D1) or NITE BP-03042 (PG4D2).

2. A neutralizing monoclonal antibody or a fragment consisting of a functional fragment thereof, wherein the monoclonal antibody according to claim 1 is chimeric or humanized.

3. A hybridoma of deposition No. NITE BP-03041 or NITE BP-03042.

4. An Aggrus-CLEC-2 binding inhibitor comprising a neutralizing monoclonal antibody or a fragment consisting of a functional fragment thereof according to claim 1.

5. A composition for inhibiting Aggrus-CLEC-2 binding, comprising:
   a neutralizing monoclonal antibody or a fragment consisting of a functional fragment thereof according to claim 1, and
   at least one monoclonal antibody, chimeric antibody thereof, humanized antibody thereof, and/or fragment consisting of a functional fragment thereof,
   wherein the monoclonal antibody is produced by a hybridoma of deposition No. FERM BP-11446 (P2-0), FERM BP-11447 (MS-1), FERM BP-11448 (MS-3) and/or FERM BP-11449 (MS-4).

6. A pharmaceutical composition for inhibition of platelet aggregation, inhibition of thrombus formation, inhibition of cancer progression or metastasis, or anti-inflammation, comprising a neutralizing monoclonal antibody or a fragment consisting of a functional fragment thereof according to claim 1.

7. The pharmaceutical composition according to claim 6, further comprising at least one monoclonal antibody, chimeric antibody thereof, humanized antibody thereof, and/or fragment consisting of a functional fragment thereof,
   wherein the monoclonal antibody is produced by a hybridoma of deposition No. FERM BP-11446 (P2-0), FERM BP-11447 (MS-1), FERM BP-11448 (MS-3) and/or FERM BP-11449 (MS-4).

8. A testing reagent for detection of Aggrus expression, comprising a neutralizing monoclonal antibody or a fragment consisting of a functional fragment thereof according to claim 1.

* * * * *

SEQUENCE LISTING

<160> NUMBER OF SEQ ID NOS: 20

<210> SEQ ID NO 1
<211> LENGTH: 9
<212> TYPE: PRT
<213> ORGANISM: Homo sapiens

<400> SEQUENCE: 1

Gly Ile Arg Ile Glu Asp Leu Pro Thr
1               5

<210> SEQ ID NO 2
<211> LENGTH: 17
<212> TYPE: PRT
<213> ORGANISM: Homo sapiens

<400> SEQUENCE: 2

Gly Ala Glu Asp Asp Val Val Thr Pro Gly Thr Ser Glu Asp Arg Tyr
1               5                   10                  15

Lys

<210> SEQ ID NO 3
<211> LENGTH: 5
<212> TYPE: PRT
<213> ORGANISM: Homo sapiens

<400> SEQUENCE: 3

Arg Ile Glu Asp Leu
1               5

<210> SEQ ID NO 4
<211> LENGTH: 6
<212> TYPE: PRT
<213> ORGANISM: Homo sapiens
<220> FEATURE:
<221> NAME/KEY: misc_feature
<222> LOCATION: (3)..(4)
<223> OTHER INFORMATION: Xaa can be any naturally occurring amino acid

<400> SEQUENCE: 4

Glu Asp Xaa Xaa Thr Ser
1               5

<210> SEQ ID NO 5
<211> LENGTH: 144
<212> TYPE: PRT
<213> ORGANISM: Homo sapiens

<400> SEQUENCE: 5

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
                20                  25                  30

Glu Thr Thr Gly Leu Glu Gly Gly Val Ala Met Pro Gly Ala Glu Asp
            35                  40                  45

Asp Val Val Thr Pro Gly Thr Ser Glu Asp Arg Tyr Lys Ser Gly Leu
        50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys

```
                    100                 105                 110
Val Asp Gly Asp Thr Gln Thr Thr Val Glu Lys Asp Gly Leu Ser Thr
                115                 120                 125

Val Thr Leu Val Gly Ile Ile Val Gly Val Leu Leu Ala Ile Gly Phe
            130                 135                 140
```

<210> SEQ ID NO 6
<211> LENGTH: 144
<212> TYPE: PRT
<213> ORGANISM: Pan paniscus

<400> SEQUENCE: 6

```
Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
                20                  25                  30

Glu Thr Thr Gly Leu Glu Gly Gly Phe Ala Val Pro Gly Ala Glu Asp
            35                  40                  45

Asp Val Val Thr Pro Gly Thr Ser Glu Asp Arg Tyr Lys Ser Gly Leu
        50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ala Thr
        115                 120                 125

Val Thr Leu Val Gly Ile Ile Val Gly Val Leu Leu Ala Ile Gly Phe
    130                 135                 140
```

<210> SEQ ID NO 7
<211> LENGTH: 144
<212> TYPE: PRT
<213> ORGANISM: Macaca mulatta

<400> SEQUENCE: 7

```
Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Ile
                20                  25                  30

Glu Thr Thr Gly Met Glu Gly Gly Val Ala Met Pro Gly Ala Glu Asp
            35                  40                  45

Asp Val Val Thr Pro Gly Thr Ser Glu Asp Arg Tyr Lys Ser Gly Leu
        50                  55                  60

Thr Thr Pro Val Ala Thr Ser Val Asn Ser Val Thr Asp Ile His Ile
65                  70                  75                  80

Glu Asp Leu Pro Thr Pro Glu Ser Thr Val His Ala Gln Gly Gln Ser
                85                  90                  95

Pro Ser Thr Thr Ala Ser Asn Val Ala Thr Ser His Ser Thr Asp Lys
            100                 105                 110

Val Asp Gly Asp Thr Gln Thr Ala Ile Glu Lys Asp Gly Leu Ala Thr
        115                 120                 125

Val Thr Leu Val Gly Ile Ile Val Gly Val Leu Leu Ala Ile Gly Phe
    130                 135                 140
```

<210> SEQ ID NO 8
<211> LENGTH: 141
<212> TYPE: PRT
<213> ORGANISM: Sus scrofa

<400> SEQUENCE: 8

Met Trp Lys Val Pro Val Leu Leu Phe Val Leu Gly Ser Ala Ser Leu
1               5                   10                  15

Trp Val Leu Ala Glu Gly Ala Ser Thr Val Leu Pro Glu Asp Gly Val
            20                  25                  30

Thr Pro Gly Val Glu Gly Ser Ser Lys Ala Ser Pro Gly Val Glu Asp
        35                  40                  45

Tyr Thr Val Thr Pro Arg Thr Arg Glu Glu Pro Tyr Ala Thr Pro Leu
    50                  55                  60

Val Pro Thr Arg Thr Lys Gly Thr Thr Gly Ser Pro Thr Glu Asp Val
65                  70                  75                  80

Phe Thr Val Gly Ser Thr Thr His Ser His Lys Gly Ser Gln Ser Thr
            85                  90                  95

Thr Thr Gln Asn Val Val Thr Ser Gln Ser His Asp Lys Gly Asp Glu
            100                 105                 110

Glu Lys Ser Lys Thr Val Thr Lys Asp Gly Leu Gly Thr Val Thr Leu
        115                 120                 125

Val Gly Ile Thr Val Gly Val Leu Leu Ala Ile Gly Phe
    130                 135                 140

<210> SEQ ID NO 9
<211> LENGTH: 143
<212> TYPE: PRT
<213> ORGANISM: Physeter catodon

<400> SEQUENCE: 9

Met Trp Lys Gly Pro Val Leu Phe Phe Val Leu Gly Ser Ala Ser Leu
1               5                   10                  15

Trp Val Leu Ala Glu Ala Ser Thr Val Arg Pro Glu Asp Gly Met Thr
            20                  25                  30

Thr Gly Val Glu Asn Gly Lys Ala Thr Pro Gly Val Glu Asp His Val
        35                  40                  45

Glu Thr Pro Gly Ala Ser Gly Glu Pro His Glu Ser Ala Gly Leu Thr
    50                  55                  60

Ala Pro Met Pro Thr Arg Thr Lys Ser Met Thr Glu Val His Lys Glu
65                  70                  75                  80

Asp Leu Pro Thr Ala Glu Ser Thr Ile His Ser Gln Gly Gln Ser Gln
            85                  90                  95

Ser Thr Thr Thr Leu Asn Val Ala Thr Ser Gln Ser Pro Gly Lys Thr
            100                 105                 110

Asp Gly Glu Lys Pro Thr Thr Val Glu Lys Gly Gly Ser Ser Thr Val
        115                 120                 125

Thr Leu Val Gly Ile Ile Val Gly Val Leu Leu Ala Ile Gly Phe
    130                 135                 140

<210> SEQ ID NO 10
<211> LENGTH: 152
<212> TYPE: PRT
<213> ORGANISM: Bos taurus

<400> SEQUENCE: 10

Met Trp Lys Val Pro Val Leu Phe Phe Ile Leu Gly Ser Ala Ser Phe
1               5                   10                  15

Trp Val Leu Ala Glu Gly Ala Ser Thr Val Arg Pro Glu Asp Val
            20                  25                  30

Thr Thr Gly Val Thr Ser Glu Lys Thr Thr Leu Gly Val Glu Asp Tyr
        35                  40                  45

Thr Thr Thr Pro Ala Ala Ser Lys Glu Ser Leu Ala Thr Pro Met Pro
50                  55                  60

Ala Gly Thr Glu Asn Val Ser His Asp His Arg Glu Asp Leu Pro Thr
65                  70                  75                  80

Ala Glu Gly Thr Thr Ala Glu Gly Thr Thr Ala Lys Ser Thr Pro Ala
                85                  90                  95

Arg Ser Thr Pro Ala Arg Ser Thr Thr Thr Val Leu Thr Arg Val Pro
            100                 105                 110

Ala Thr Ser His Ser Gln Gly Lys Thr Asp Gly Glu Lys Pro Lys Ser
            115                 120                 125

Thr Gln Lys Gly Gly Leu Ser Val Gly Thr Leu Val Gly Ile Ile Val
        130                 135                 140

Gly Val Leu Val Gly Ile Ala Val
145                 150

<210> SEQ ID NO 11
<211> LENGTH: 151
<212> TYPE: PRT
<213> ORGANISM: Canis lupus

<400> SEQUENCE: 11

Met Trp Arg Val Pro Val Leu Leu Leu Val Leu Gly Gly Ala Gly Leu
1               5                   10                  15

Arg Val Pro Ala Ala Gly Ala Ser Thr Val Arg Pro Asp Asp Ile Ile
            20                  25                  30

Pro Gly Val Glu Asp Ser Val Val Thr Pro Gly Thr Glu Asp Ser Val
        35                  40                  45

Val Thr Pro Gly Ala Glu Asp Asn Val Val Thr Asp Gly Ala Thr Glu
    50                  55                  60

Glu Pro Tyr Glu Ser Gly Leu Thr Pro Leu Val Thr Lys Asn Thr Glu
65                  70                  75                  80

Ser Val Thr Asp Leu His Leu Glu Asp Gly Pro Thr Gln Glu Ser Thr
                85                  90                  95

Val His Ala Lys Glu Glu Ser Gln Ser Thr Thr Thr Leu Asn Val Val
            100                 105                 110

Thr Ser His Ser Arg Glu Lys Val Gly Glu Asp Thr Glu Thr Thr Val
            115                 120                 125

Glu Lys Asp Gly Leu Ala Thr Val Thr Val Gly Ile Ile Val Gly
        130                 135                 140

Val Leu Leu Ala Ile Gly Phe
145                 150

<210> SEQ ID NO 12
<211> LENGTH: 140
<212> TYPE: PRT
<213> ORGANISM: Myotis bechsteini

<400> SEQUENCE: 12

Met Trp Lys Ala Arg Val Leu Leu Leu Val Trp Gly Ser Ala Leu Leu
1               5                   10                  15

Trp Ala Pro Ala Gly Gly Ala Ser Thr Val Leu Pro Glu Asp Glu Ala
            20                  25                  30

```
Thr Thr Ala Ser Met Glu Asn Gly Met Val Thr Pro Gly Val Gly
            35                  40                  45

Asn Thr Met Thr Pro Gly Ala Ser Glu Gln Ser His Lys Pro Val Gly
 50                  55                  60

Phe Thr Ser Gln Val Pro Thr Asn Thr Lys Arg Thr Asp Thr Pro Ile
 65                  70                  75                  80

Glu Asp Leu Pro Thr Thr Glu Ser Thr Gly His Ala Gln Glu Thr
                85                  90                  95

Gln Ser Thr Thr Ala Leu Asn Gly Ala Thr Ser His Pro Arg Glu Asp
                100                 105                 110

Thr Gln Thr Thr Gly Ala Lys Asp Gly Phe Ser Thr Gly Thr Leu Ile
                115                 120                 125

Gly Ile Ile Val Gly Val Leu Leu Gly Ile Gly Phe
    130                 135                 140

<210> SEQ ID NO 13
<211> LENGTH: 148
<212> TYPE: PRT
<213> ORGANISM: Rattus norvegicus

<400> SEQUENCE: 13

Met Trp Thr Ala Pro Val Leu Leu Trp Val Gly Ser Val Trp Phe
 1               5                  10                  15

Trp Asp Ser Ala Gln Gly Gly Ala Ile Gly Ala Leu Glu Asp Asp Leu
                20                  25                  30

Val Thr Pro Gly Pro Gly Asp Asp Met Val Asn Pro Gly Leu Glu Asp
                35                  40                  45

Arg Ile Glu Thr Thr Asp Thr Thr Gly Glu Leu Asp Lys Ser Thr Ala
 50                  55                  60

Lys Ala Pro Leu Val Pro Thr Gln Pro Pro Ile Glu Glu Leu Pro Thr
 65                  70                  75                  80

Ser Gly Thr Ser Asp His Asp His Lys Glu His Glu Ser Thr Thr Thr
                85                  90                  95

Val Lys Ala Val Thr Ser His Ser Thr Asp Lys Lys Thr Thr His Ser
                100                 105                 110

Asn Arg Asp Asn Ala Gly Gly Glu Thr Gln Thr Thr Asp Lys Lys Asp
                115                 120                 125

Gly Leu Ala Val Val Thr Leu Val Gly Ile Ile Gly Val Leu Leu
                130                 135                 140

Ala Ile Gly Phe
145

<210> SEQ ID NO 14
<211> LENGTH: 154
<212> TYPE: PRT
<213> ORGANISM: Mus musculus

<400> SEQUENCE: 14

Met Trp Thr Val Pro Val Leu Phe Trp Val Gly Ser Val Trp Phe
 1               5                  10                  15

Trp Asp Ser Ala Gln Gly Gly Thr Ile Gly Val Asn Glu Asp Asp Ile
                20                  25                  30

Val Thr Pro Gly Thr Gly Asp Gly Met Val Pro Pro Gly Ile Glu Asp
                35                  40                  45

Lys Ile Thr Thr Thr Gly Ala Thr Gly Gly Leu Asn Glu Ser Thr Gly
 50                  55                  60
```

```
Lys Ala Pro Leu Val Pro Thr Gln Arg Glu Arg Gly Thr Lys Pro Pro
 65                  70                  75                  80

Leu Glu Glu Leu Ser Thr Ser Ala Thr Ser Asp His Asp His Arg Glu
             85                  90                  95

His Glu Ser Thr Thr Thr Val Lys Val Val Thr Ser His Ser Val Asp
            100                 105                 110

Lys Lys Thr Ser His Pro Asn Arg Asp Asn Ala Gly Asp Glu Thr Gln
        115                 120                 125

Thr Thr Asp Lys Lys Asp Gly Leu Pro Val Val Thr Leu Val Gly Ile
    130                 135                 140

Ile Val Gly Val Leu Leu Ala Ile Gly Phe
145                 150

<210> SEQ ID NO 15
<211> LENGTH: 8
<212> TYPE: PRT
<213> ORGANISM: Homo sapiens
<220> FEATURE:
<221> NAME/KEY: misc_feature
<222> LOCATION: (3)..(4)
<223> OTHER INFORMATION: Xaa can be any naturally occurring amino acid

<400> SEQUENCE: 15

Glu Asp Xaa Xaa Val Thr Pro Gly
1               5

<210> SEQ ID NO 16
<211> LENGTH: 8
<212> TYPE: PRT
<213> ORGANISM: Homo sapiens

<400> SEQUENCE: 16

Glu Asp Asp Thr Glu Thr Thr Gly
1               5

<210> SEQ ID NO 17
<211> LENGTH: 8
<212> TYPE: PRT
<213> ORGANISM: Homo sapiens

<400> SEQUENCE: 17

Glu Gly Gly Val Ala Met Pro Gly
1               5

<210> SEQ ID NO 18
<211> LENGTH: 8
<212> TYPE: PRT
<213> ORGANISM: Homo sapiens

<400> SEQUENCE: 18

Glu Asp Asp Val Val Thr Pro Gly
1               5

<210> SEQ ID NO 19
<211> LENGTH: 7
<212> TYPE: PRT
<213> ORGANISM: Homo sapiens

<400> SEQUENCE: 19

Glu Asp Leu Pro Thr Ser Glu
1               5
```

```
<210> SEQ ID NO 20
<211> LENGTH: 162
<212> TYPE: PRT
<213> ORGANISM: Homo sapiens

<400> SEQUENCE: 20

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
            20                  25                  30

Glu Thr Thr Gly Leu Glu Gly Gly Val Ala Met Pro Gly Ala Glu Asp
        35                  40                  45

Asp Val Val Thr Pro Gly Thr Ser Glu Asp Arg Tyr Lys Ser Gly Leu
    50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ser Thr
            115                 120                 125

Val Thr Leu Val Gly Ile Ile Val Gly Val Leu Leu Ala Ile Gly Phe
            130                 135                 140

Ile Gly Gly Ile Ile Val Val Met Arg Lys Met Ser Gly Arg Tyr
145                 150                 155                 160

Ser Pro
```